(12) United States Patent
Wang et al.

(10) Patent No.: US 8,106,080 B2
(45) Date of Patent: Jan. 31, 2012

(54) COMPOSITIONS AND METHODS FOR ENHANCING NITRIC OXIDE DELIVERY

(76) Inventors: Gu-Qi Wang, Winnipeg (CA); Frank J Burczynski, Winnipeg (CA); Judith E Anderson, Winnipeg (CA)

( * ) Notice: Subject to any disclaimer, the term of this patent is extended or adjusted under 35 U.S.C. 154(b) by 1088 days.

(21) Appl. No.: 11/916,912

(22) PCT Filed: Jun. 8, 2006

(86) PCT No.: PCT/CA2006/000942
§ 371 (c)(1),
(2), (4) Date: Dec. 7, 2007

(87) PCT Pub. No.: WO2006/130982
PCT Pub. Date: Dec. 14, 2006

(65) Prior Publication Data
US 2008/0207713 A1    Aug. 28, 2008

(51) Int. Cl.
C07C 203/04 (2006.01)
A61K 31/21 (2006.01)
A61K 31/421 (2006.01)
A61K 31/075 (2006.01)
A61K 31/4166 (2006.01)
A61K 31/343 (2006.01)
A61K 31/04 (2006.01)
A61K 31/13 (2006.01)
A61K 31/16 (2006.01)

(52) U.S. Cl. ........ 514/375; 514/479; 514/718; 514/390; 514/470; 514/740; 514/741; 514/674; 514/626

(58) Field of Classification Search .................. 514/375, 514/479, 718, 390, 470, 740, 674, 626, 741
See application file for complete search history.

(56) References Cited

PUBLICATIONS

Anderson, "A Role for Nitric Oxide in Muscle Repair: Nitric Oxide-mediated Activation of Muscle Satellite Cells" (2000) Molec. Biol. Cell 11 (5) : 1859-1874.
Anderson and Pilipowicz, Activation of Muscle Satellite Cells in Single-fiber Cultures (2002) Nitric Oxide 7:36-41.
Anderson and Vargas, Correlated NOS-Iμ and myf5 Expression by Satellite Cells in mdx Mouse Muscle Regeneration During NOS Manipulation and Deflazacort Treatment (2003) Neuromuscular Disorders 13:388-396.
Anderson and Wozniak, Satellite Cell Activation on Fibers: Modeling Events In Vivo—an Invited Review (2004) Can. J. Physiol. Pharmacol. 82:300-310.
Chen et at ., "Vanidil: A Newly Synthesized Antiangina Nonvolatile Organic Solid Nitrate" (1991) Gaoxiong Yi Xue Ke Xue Za Zhi . 7(9) : 476-80.
Chen et al., "J-based 2D Homonuclear and Heteronuclear Correlation in Solid-state Proteins" Mag. Reson. Chem. 2007; 45:S-84-92.
Collins, C.A. et al., "Stem Cell Function, Self-renewal, and Behavioral Heterogeneity of Cells From the Adult Muscle Satellite Cell Niche" Cell 122: 289-301; 2005.
Jung et al ., "Multi-frequency EPR and Mössbauer Spectroscopic Studies on Freeze-quenched Reaction Intermediates of Nitric Oxide Synthase" Magn. Reson. Chem. 2005; 43: Spec. No. S84-95.
Megson, "Nitric Oxide Donor Drugs" (2000) Drugs of the Future. 25 (7) : 701-715.
Pchelka, B.K. et al., "Resolution of Racemic 3-aryloxy-1-nitrooxypropan-2-ols by Lipase-catalyzed Enantioselective Acetylation" Tetrahedron: Asymmetry (2001), 12, 2109-2119. (D4 on ISR).
Tatsumi et al., "Release of Hepatocyte Growth Factor From Mechanically Stretched Skeletal Muscle Satellite Cells and Role of pH and Nitric Oxide" (2002) Molec. Biol. Cell 13:2909-2918.
Wozniak et al., "Signaling Satellite-cell Activation in Skeletal Muscle: Markers, Models, Stretch, and Potential Alternate Pathways" (2005) Muscle & Nerve 31:283-300.
Zhou et al., "Detection of Nitric Oxide in Tissue by Spin Trapping EPR Spectroscopy and Triacetyiglycerol Extraction" Biotechnology Techniques 1999; 13: 507-511.

*Primary Examiner* — Jason Sims
*Assistant Examiner* — Zohreh Vakili
(74) *Attorney, Agent, or Firm* — Ade & Company Inc.; Michael R. Williams

(57) ABSTRACT

The present invention is directed to compounds, combinations, compositions and methods for enhancing nitric oxide (NO) delivery to target sites, and in particular to muscle, both normal and dystrophic. Enhanced NO delivery according to the present invention may be achieved by using a combination of a muscle relaxant and an NO donor compound, or by using a compound of the invention: formula (I) wherein $R^1$ is H, halo, $C_{1-6}$ alkoxy or $C_{1-6}$ alkyl; $R^2$ is H, $NO_2$ or $C(O)NH_2$; $R^3$ is H, $NO_2$ or $C(O)NH_2$; and at least one of $R^2$ and $R^3$ is $NO_2$; or a pharmaceutically acceptable salt of the compound.

(I)

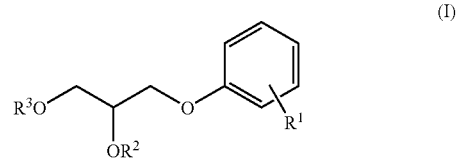

13 Claims, 18 Drawing Sheets

COMPOSITIONS AND METHODS FOR ENHANCING NITRIC OXIDE DELIVERY

The present invention relates generally to enhancing nitric oxide (NO) delivery to target sites to increase cell proliferation, in particular in muscle cells, or to repair damaged muscle tissue in normal and disease states. Compounds, combinations and compositions comprising nitric oxide donors are disclosed.

BACKGROUND

Muscle tissue in adult vertebrates regenerates from reserve cells or stem cells or inactive myoblasts called satellite cells. Satellite cells are distributed throughout muscle tissue in close juxtaposition to muscle fibers, and are mitotically quiescent in adult muscle when injury, disease or muscle growth is absent.

Following muscle fiber injury or during the process of recovery from disease, satellite cells re-activate and re-enter the cell cycle. Once activated, the satellite cells proliferate and the daughter cells (progeny cells termed myoblasts) either 1) fuse with existing multinucleated muscle fibers to contribute new nuclei that support muscle growth or regeneration, or 2) fuse with one another to form a new length of multinucleated muscle fiber called a myotube. The new piece (or segment) of a muscle fiber then differentiates into a mature muscle fiber segment that can contract and produce force. If a completely new myotube was formed from the fusion of myoblasts, that myotube then differentiates into a new fiber. The myoblasts therefore ultimately yield replacement muscle fibers or fuse into existing muscle fibers, thereby increasing fiber girth or length or both length and girth. Satellite cells of normal skeletal muscle provide a constant and renewable source of myogenic precursor cells which allows for skeletal muscle repair and regeneration throughout mammalian life.

Nitric oxide (NO), an inorganic free radical, is a versatile biological messenger. Endogenous NO is synthesized from the amino acid L-arginine by three isoforms of the enzyme NO synthase (NOS). Potential pathways of NO signaling in skeletal muscle are reviewed in Anderson and Wozniak (2004) Can. J. Physiol. Pharmacol. 82:300-310, and Wozniak et al. (2005) Muscle & Nerve 31:283-300.

Endogenous NO is a key messenger molecule in the cardiovascular, nervous and immune systems. Research to date has centred largely on the cardiovascular system in which reduced bioavailability of NO is implicated in a range of diseases. A number of NO donors have been used in cardiovascular medicine, including organic nitrates or nitrites, such as amyl nitrite, glyceryl trinitrate and isosorbide dinitrate (ISDN) (see Megson (2000) Drugs of the Future. 25(7):701-715). A compound called vanidil (4-O-(1,2-dinitroglyceryl)-6-nitrovanillic acid) has been synthesized and suggested for use in treating angina (Chen et al. (1991) Gaoxiong Yi Xue Ke Xue Za Zhi. 7(9):476-80).

We previously showed that NO mediates satellite cell activation, and proposed that NO release mediates satellite cell activation possibly via shear-induced rapid increases in NOS activity that produce NO transients; see Anderson (2000) Molec. Biol. Cell 11(5):1859-1874, Tatsumi et al. (2002) Molec. Biol. Cell 13:2909-2918, Anderson and Vargas (2003) Neuromuscular Disorders 13:388-396, and Anderson and Pilipowicz (2002) Nitric Oxide 7:36-41.

Since musculoskeletal health is exquisitely dependent on growth and repair, developing a system to deliver NO to skeletal muscle and thereby manipulate the regulation of satellite cell activation has the potential to promote normal function in injured muscle tissue and possibly be used to treat neuromuscular disease. Furthermore, targeting NO delivery would help avoid side effects in reproductive, vascular and nerve tissue where NO signaling also regulates function.

SUMMARY

According to one aspect of the invention, there is provided a combination of a muscle relaxant and a nitric oxide (NO) donor. In an exemplary embodiment, the combination is provided in a composition, together with a pharmaceutically acceptable diluent or carrier.

According to another aspect of the invention, there is provided a pharmaceutical composition comprising an effective amount of a combination of a muscle relaxant and an NO donor; and a pharmaceutically acceptable diluent or carrier for promoting muscle cell proliferation or repair in normal (i.e., non-dystrophic) muscle in need thereof.

According to a further aspect of the invention, there is provided a pharmaceutical composition comprising an effective amount of a combination of a muscle relaxant and an NO donor; and a pharmaceutically acceptable diluent or carrier for regulating satellite cell proliferation in dystrophic muscle.

According to a still further aspect of the invention, there is provided a pharmaceutical composition comprising an effective amount of a combination of a muscle relaxant and an NO donor; and a pharmaceutically acceptable diluent or carrier for treating muscular dystrophy.

In one embodiment of the invention, the muscle relaxant is a centrally acting skeletal muscle relaxant, such as methocarbamol, chlorphenesin, chlorphenesin carbamate, chlorzoxazone, guaifenesin, carisoprodol, mephenesin, meprobamate, dantrolene or 3-phenoxy-1,2-propanediol; or a pharmaceutically acceptable salt thereof. In an exemplary embodiment, the muscle relaxant is methocarbamol.

In another embodiment, the NO donor is an organic nitrate, an O-nitrosylated compound, an S-nitrosylated compound, a diazeniumdiolate, an organic nitrite, or an inorganic nitroso compound. In exemplary embodiments, the NO donor is isosorbide dinitrate, nitroglycerin, diethylenetriamine-NONOate, dipropylenetriamine-NONOate, or S-nitrosoglutathione.

In another embodiment of the invention, the combination is provided as a single compound, such as:

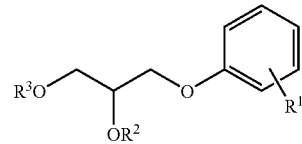

wherein $R^1$ is H, halo, $C_{1-6}$ alkoxy or $C_{1-6}$ alkyl; $R^2$ is H, $NO_2$ or $C(O)NH_2$; $R^3$ is H, $NO_2$ or $C(O)NH_2$; and at least one of $R^2$ and $R^3$ is $NO_2$; or a pharmaceutically acceptable salt of the compound.

The present invention also relates to a compound of formula:

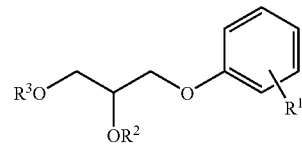

wherein $R^1$ is H, halo, $C_{1-6}$ alkoxy or $C_{1-6}$ alkyl; $R^2$ is H, $NO_2$ or $C(O)NH_2$; $R^3$ is H, $NO_2$ or $C(O)NH_2$; and at least one of $R^2$ and $R^3$ is $NO_2$; or a pharmaceutically acceptable salt of the compound.

In one embodiment, $R^1$ is in the ortho position and is methyl or methoxy. In another invention embodiment, $R^1$ is in the para position and is chloro. In a further invention embodiment, $R^1$ is hydrogen.

The present invention also relates to a compound of formula:

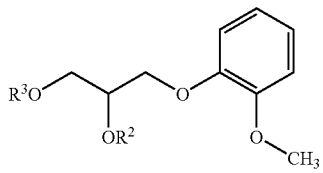

wherein $R^2$ is H, $NO_2$ or $C(O)NH_2$; $R^3$ is H, $NO_2$ or $C(O)NH_2$; and at least one of $R^2$ and $R^3$ is $NO_2$; or a pharmaceutically acceptable salt thereof.

The present invention also relates to the compound:

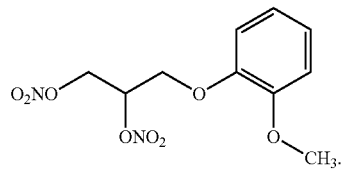

The present invention also provides a pharmaceutical composition comprising the compound or salt, and a pharmaceutically acceptable carrier. The pharmaceutical composition may be used for promoting formation of muscle tissue or promoting repair of damaged muscle tissue in normal (i.e., non-dystrophic) muscle or for regulating satellite cell proliferation in dystrophic muscle. In one invention embodiment, the composition may be used for treating muscular dystrophy.

In an exemplary embodiment, the pharmaceutical compositions of the invention are suitable for transdermal delivery, such as in the form of a topical cream.

Pharmaceutical compositions of the invention may be contained in a commercial package, together with instructions for the use thereof.

According to yet a further aspect, there is provided a method for promoting formation of muscle tissue or repair of damaged muscle tissue, the method comprising administering a compound, combination or pharmaceutical composition of the invention to a subject.

According to a still further aspect, there is provided a method for facilitating transdermal delivery of an NO donor to a target site in a subject, the method comprising applying a muscle relaxant to a skin region of the site along with application of an NO donor.

The compounds, combinations and compositions of the invention may be used in treating human or non-human animals, such as fish, reptiles, birds, dogs, horses, cats, pigs, cattle, sheep, etc.

The present invention also relates to the use of the combinations and compounds of the invention in the manufacture of a medicament.

The present invention also relates to methods of preparing compounds of the invention.

Because NO is such a versatile biological messenger having roles in the cardiovascular, nervous and immune systems, the combinations, compounds and compositions of the invention may also be useful in treating conditions where the presence of NO is expected to be of benefit, e.g., to prevent restenosis following angioplasty, to inhibit platelets to prevent coagulation and thrombus formation, and to treat angina. The combinations, compounds and compositions may also have additional therapeutic utility in cancer, killing microbes and viruses, relaxing airways and intestinal smooth muscle (e.g., for treating asthma and esophageal spasms), in promoting erectile function and in treatment of heart failure and urinary incontinence.

DETAILED DESCRIPTION

Figure 1:
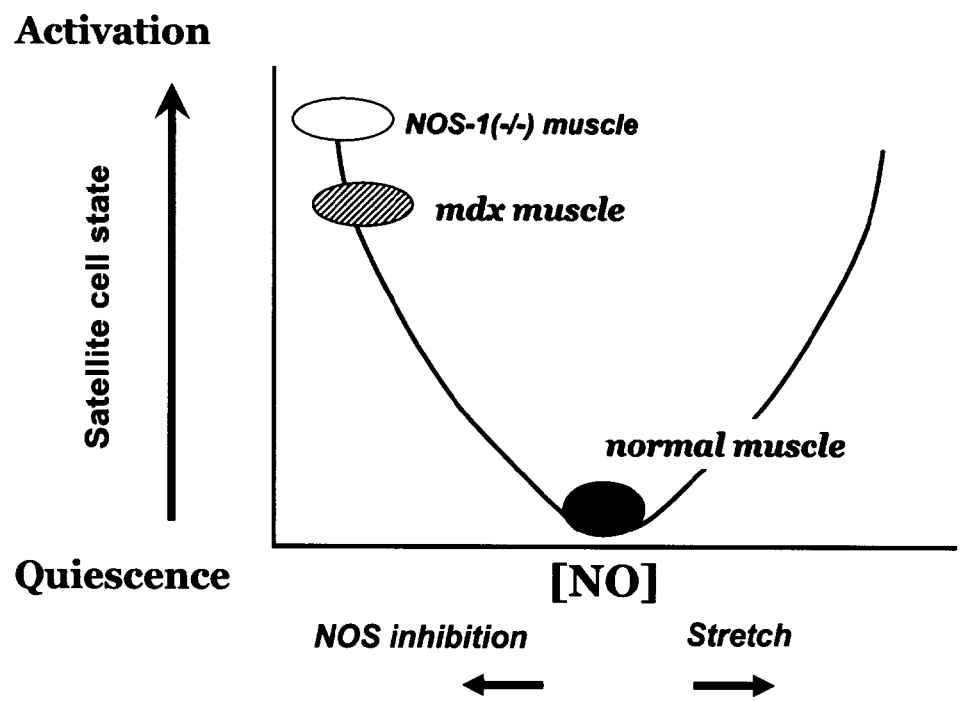
FIG. 1 is a graphic depiction of a model of satellite cell activation as a function of NO concentration within the physiological range in skeletal muscle.

As used herein, the term "myogenic precursor cells" refers to cells capable of myogenesis, or the process of proliferation and differentiation into new and functional muscle when present in a morphogenically permissive environment. Myogenic precursor cells are variously referred to as "myoblasts," "muscle stem cells" or "satellite cells".

Role of Nitric Oxide in Satellite Cell Activation

Nitric oxide (NO) is a major, freely-diffusible, endogenous mediator involved in diverse developmental and physiological processes. In addition to controlling diverse cellular processes, NO also participates in certain pathophysiological conditions. In skeletal muscle NO has been shown to depress the muscle contractile function in a manner of protecting muscle against excess strain or injury, by modulating a moderate reduction the force of contraction and increasing the time required for muscle relaxation. In the brain, nitric oxide plays important physiological roles in neurotransmission and synaptic modulation. In primary cortical cultures, NO mediates glutamate neurotoxicity.

NO has also been found to mediate the rapid activation of satellite precursor cells to enter the cell cycle. (See Anderson J E. A role for nitric oxide in muscle repair: nitric oxide-mediated activation of muscle satellite cells. Molecular Biology of the Cell 2000; 11: 1859-1874.) Such cycling provides new precursor cells for skeletal muscle growth and muscle repair from injury or disease.

Satellite cells are quiescent precursors in normal skeletal muscle. Satellite cell activation from the normal state of mitotic and metabolic quiescence is a process that occurs very rapidly (within 10 minutes in vivo) and is an important step in initiating muscle growth and repair. NO is the signal that mediates that rapid activation. Decreased NO production therefore abrogates the early phase or timing of satellite cell activation. Reduced NO production or release, therefore, impairs muscle repair in normal muscle as shown in Anderson J E. A role for nitric oxide in muscle repair: nitric oxide-mediated activation of muscle satellite cells. Molecular Biology of the Cell 2000; 11: 1859-1874 and confirmed in Collins, C. A.; Olsen, I.; Zammit, P. S.; Heslop, L.; Petrie, A.; Partridge, T. A.; Morgan, J. E. Stem cell function, self-renewal, and behavioral heterogeneity of cells from the adult muscle satellite cell niche. Cell 122: 289-301; 2005.

We hypothesise that satellite cell activation after skeletal muscle injury in normal muscle may occur as follows.

In undamaged muscle with normal contraction and relaxation, thin quiescent satellite cells are demarcated by m-cadherin and contain few organelles. They are interposed between the overlying external lamina and the sarcolemma of a subjacent fiber, and are subject to a small-amplitude pulsatile release of NO from NOS-Iµ (the skeletal muscle specific isoform of NOS) that is anchored to syntrophin in the dystrophin-associated glycoprotein complex of the subsarcolemmal cytoskeleton. Normally, NO diffuses cylindrically out from the fiber to act on cells and enzymes in the interstitium or is neutralized by red cell hemoglobin in the vessels that wrap each fiber. NO also diffuses cylindrically from NOS-Iµ inward within the fiber.

After sarcolemmal injury that exceeds the capacity of the fiber to rapidly re-seal the membrane by membrane recycling processes, depolarization of the fiber is not followed by repolarization since the membrane is required to be intact to maintain polarization. A single large contraction resulting from a rapid influx of extracellular calcium produces intense shear between the fiber membrane and external lamina. Shear induces a bolus release of NO that diffuses down its concentration gradient through the satellite cells hugging the fiber. Satellite cells become activated, and begin to enlarge as organelles such as mitochondria hypertrophy. HGF/SF (hepatocyte growth factor/scatter factor) from the extracellular matrix surrounding the damaged fiber is activated and released from the fiber matrix by the interaction with NO, shifts to the c-met receptor on satellite cells. Fibrils hypercontract and damaged segments retract within the external lamina, maintaining shear and NO release and activating cells along the fiber length. The adhesiveness of m-cadherin decreases and the damaged fiber releases proteins including HGF/SF to the interstitium. A released factor like HGF/SF, enters the circulation and can transiently activate distant satellite cells on undamaged muscles, although the normal pulsatile NO release in undamaged muscle will mostly attenuate that response. Capillaries dilate and blood cells extravasate cells into the interstitium of the damaged muscle.

Fiber segments fully retract and satellite cells become motile precursors as HGF/SF binds to c-met, a receptor with known actions to regulate cell motility. The external lamina remains as a scaffold for the satellite cells, now surrounded by less adhesive m-cadherin. The precursors may leave the fiber as the sequential expression of early immediate genes, delayed early genes, muscle regulatory genes, proliferating cell nuclear antigen and later DNA synthesis begin prior to cell proliferation.

Similar to fiber damage through an injurious contraction of the fiber, stretching a muscle or muscle fiber also causes NO release and satellite cell activation. In this case, stretching a muscle in vivo in living animals, or in whole muscles maintained in tissue culture or intact single isolated muscle fibers maintained in tissue culture, also causes release of NO and leads to: HGF release, satellite cell activation from quiescence, and entry into proliferation. Inhibition of NOS activity using a NOS inhibitor such as L-NAME (L-nitro-arginine methyl ester), prevents that stretch-related NO release and NO-dependent HGF release, thus preventing satellite cell activation.

On the other hand, in Duchenne muscular dystrophy (DMD), an X-linked recessive disorder characterized by progressive and lethal muscle weakness, and in its genetic murine homologue the mdx mouse, dystrophin and dystrophin-associated glycoproteins are absent from the sub-sarcolemmal cytoskeleton complex. The deficiencies essentially weaken the fiber sarcolemma, increasing its susceptibility to contraction-induced fiber damage which initiates segmental fiber necrosis and focal inflammation. In the mdx mouse limb and respiratory muscles including the thoracic diaphragm muscle, the resulting sequential regeneration processes are relatively effective over the short-to-medium term in the lifespan of the mouse, in that muscle function is nearly restored, although the muscles are enlarged to compensate for persistent weakness (measured as specific force, which is the calculated force measurement produced per unit muscle mass or per unit muscle cross-sectional area). In the longer term, the dystrophic muscles of mdx mice are unable to sustain the requirement for regeneration processes following ongoing fiber damage, and the disease induces progressively more severe weakness in limb and respiratory muscles which results in early death, similar to although less rapid and less severe than the disease progression at in DMD.

In relation to muscular dystrophy, we hypothesise that the NOS-Iµ which displaced to the cytoplasm in mdx muscle would act as a diffuse areal source of NO rather than the nearby cylindrical source (or viewed in a tissue section, a linear source) that is confined as a source in the cytoskeleton subjacent to the sarcolemma and parallel to the overlying satellite cells found in normal muscle. The normally steep NO gradient across the cleft between fiber and satellite cell (between membrane-associated cylindrical-source of NOS-Iµ and the topographically adjacent cell) would therefore be more shallow, diffuse more slowly, and the small NO transient would show attenuated responsiveness to shear forces.

We have observed the character of NO release by stretching muscle myotubes that were formed in tissue culture from preparations of myogenic cells from normal and mdx mouse muscle, and shown that this predicted change is real. Since normal pulsatile NO acts to maintain quiescence, a smaller gradient from pulsatile NO of cytoplasmic origin in dystrophy could release mdx satellite cells from what is normally full quiescence, and account for the greater proliferative activity and larger (that is, more activated) satellite cells in mdx muscle and primary cultures. Rapid repair by mdx muscle is consistent with the notion that mdx satellite cells are partly activated or on 'stand-by.'

The resulting very shallow gradient or physiological NO transient across satellite cells could thus account partly for the severity of Duchenne dystrophy. It is as though the standby activation (like a "hair trigger") contributes to overly enthusiastic or overly vigorous successive repair events and resulting in premature senescence of dystrophic muscle precursor cells.

We think it is the differences in activation status between dystrophic and normal muscle in combination with increasing fibrosis in the connective tissue between dystrophic fibers in skeletal muscle, that contribute a large part of the eventual incapacity of the dystrophic muscle to regenerate muscle tissue. We believe that as dystrophic damage and tissue repair processes are ongoing in muscular dystrophy, the available pool of myogenic precursor or stem or satellite cells becomes exhausted.

Based on the above hypotheses, we expect that the effects of NO delivery to normal and dystrophic muscle to be different. Treatments acting via NO are expected to stimulate activation of normal skeletal muscle satellite cells from their quiescent state (the normal state in adult muscle), promoting growth and regeneration in normal cells. In dystrophic muscle, NO delivery is expected to benefit skeletal muscle by partly or fully restoring satellite cells in dystrophic muscle toward the normal pattern of regulation of satellite cell activation (and subsequent proliferation and DNA synthesis).

Accordingly, in dystrophic muscle, treatments acting via NO should act by regulating the hyper-activated muscle precursor cells from their activated state toward a more quiescent state in the absence of direct damage to the fibers on which they reside in the muscle tissue. This will likely be observed as a reduction in DNA synthesis and/or a prevention of the hyper-activated state (i.e., the 'hair trigger' or 'on call' state) which characterizes the activation state of dystrophic muscle.

In fact, the results of our experiments support the above hypotheses. It was observed that delivery of a NO donor compound to normal and dystrophic muscle had the effect of, in the case of normal muscle, increasing DNA synthesis, and for dystrophic muscle, decreasing DNA synthesis. An increase in DNA synthesis is evidence of satellite cell activation, and a decrease in DNA synthesis is evidence of satellite cell deactivation.

According to experiments conducted, a model of NO activation of satellite cells within the physiological range of NO is proposed (FIG. 1). Without being bound by any theory, the model proposes satellite cell activation as a U-shaped function of NO concentration: normally low [NO] maintains quiescence; higher [NO] (e.g., from stretch-induced NO release) induces activation; and low [NO] (e.g., in mdx muscle, NOS-I$^{(-/-)}$ muscle, and after NOS inhibition by L-NAME) also induces activation. According to this model, increasing NO in normal muscle from a theoretical concentration which is not identified and which would likely vary among different skeletal muscles, would increase satellite cell activation thereby promoting muscle cell proliferation and repair, while reducing NO in dystrophic muscle would decrease satellite cell activation thereby mitigating the effects of muscular dystrophy.

It is worth noting that according to this model, while NOS inhibition looks like a potential treatment to induce activation and promote repair, it inhibits myoblast fusion, impedes repair and exacerbates mdx dystrophy.

Figure 2:
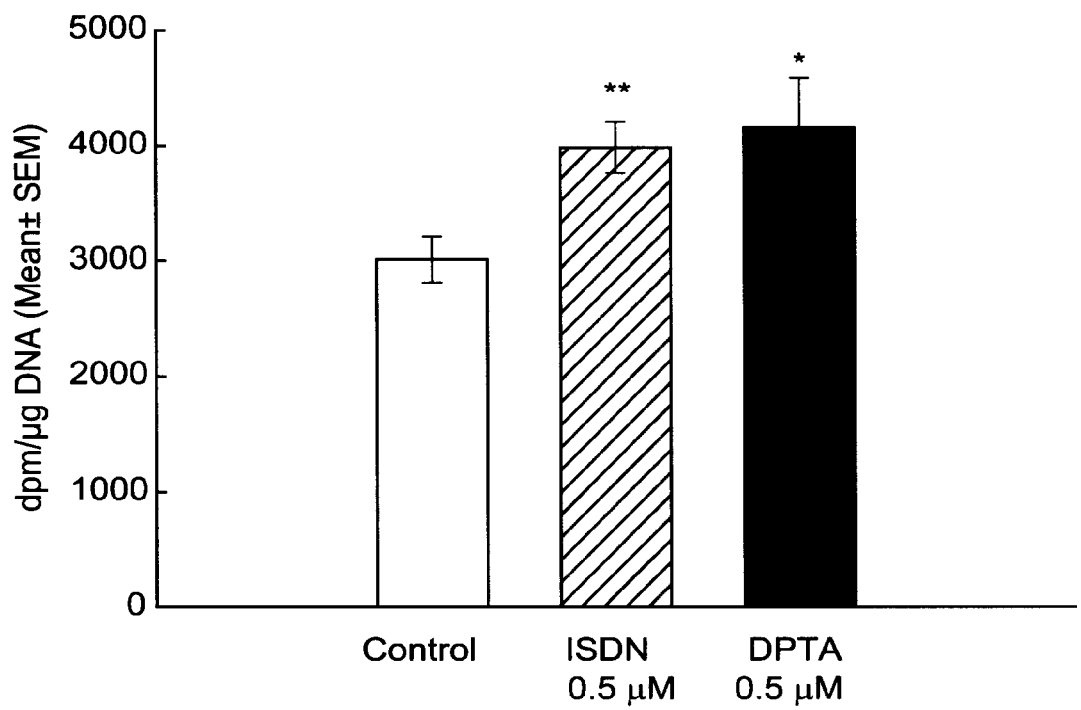
FIG. 2 is a graph of results of experiments showing the effect of two known NO donors, isosorbide dinitrate (ISDN) and dipropylenetriamine-NONOate (DPTA), on DNA synthesis by the cells of normal (C57Black/6) mouse extensor digitorum longus (EDL) muscles in a whole-muscle culture preparation.

The proposed model of satellite cell activation as a function of NO is supported by a study of the effect of two known NO donor compounds-ISDN and DPTA-on whole mouse EDL-muscle cultures (FIG. 2), which studies were performed using in vitro methods described below. Results are reported in dpm ("disintegrations per minute") per amount of DNA (here µg). This data supports the hypothesis that NO donors stimulate muscle cell activation. ISDN and DPTA, which are known to work in different mechanisms to increase NO, are both shown to stimulate an increase in DNA synthesis as evidenced by 3H-thymidine incorporation, assayed as counts per microgram DNA compared to a control muscle. In all cases, each sample was assayed in duplicate for counts, and in triplicate for DNA content (micrograms), the latter according to a standard curve of 5 or more standard concentrations that was established with a regression line having $r^2$ in the linear regression analysis greater than 0.97 at each assay.

In the present invention, it has been observed that a combination of a muscle relaxant and an NO donor compound can give enhanced delivery of NO to a target site.

No Donor Compounds

NO donor compounds for use in the present invention include not only compounds that themselves release nitric oxide, but also those compounds that are NO releasing substrates. Thus, NO donor compounds include those compounds that release nitric oxide with or without the activity of an enzyme or otherwise directly or indirectly deliver or transfer nitric oxide to a site of its activity, such as to a cell membrane, in vivo.

As used here, the term "nitric oxide" encompasses uncharged nitric oxide (NO•) and charged nitric oxide species, particularly including nitrosonium ion (NO+) and nitroxyl ion (NO−).

Without limitation, NO donor compounds include:
organic nitrates (organic compounds having a >C—ONO$_2$ group) such as isosorbide dinitrate, glyceryl trinitrate (GTN), nitroglycerin and sinitrodil;
O-nitrosylated compounds (organic compounds having a —O—NO group), also sometimes referred to as organic nitrites such as isoamyl nitrite;
inorganic nitroso compounds (inorganic compounds having a —NO group), such as sodium nitroprusside;
NONOates (compounds having an —NONO group), also known as diazeniumdiolates, such as diethylenetriamine-NONOate (DETA) and dipropylenetriamine-NONOate (DPTA);
S-nitrosylated compounds (compounds having a —S—NO group), such as S-nitrosoglutathione;
sydnonimines, such as molsidomine or its metablolite 3-morpholinosydnonomine;
furoxans;
mesoionic oxatriazole derivatives, including:

iron-sulphur nitrosyls, such as Rossin's black salt, Na$^+$ [Fe$_4$S$_3$(NO)$_7$]; and
FK-409 and its derivatives, including FR-144420:

L-arginine may also be used in providing NO. L-arginine is not itself an NO donor, but is an NOS substrate, and, as such, is indirectly useful in providing NO.

NO donors may also be made by a hybridization of NO-donor moieties with known cardiovascular drugs. One such example is S-nitrosocaptopril (SNOCap) which combines NO donor properties with an inhibitory effect on angiotensin converting enzyme (ACE). Other examples include NCX-4016, an aspirin/nitrate hybrid, and the calcium antagonist, 4-phenyl-1,4-dihydropyridines, linked to NO-donating furoxans.

For a review of NO donor compounds see Megson 2000. Drugs of the Future. 25(7):701-715.

Pharmaceutically acceptable salts of known NO donor compounds may also be used in the compositions, methods and uses of the present invention.

It is understood that the appropriate choice of NO donor compound may facilitate its transport, prolong its life in the target tissues, target its delivery to specific sites (e.g. skeletal muscle) and mitigate its potential cytotoxicity. Different NO donor compounds have different rates of release, and different mechanisms of release (i.e., non-enzymatic and enzymatic) which may dictate suitability for a given application.

Muscle Relaxants

Muscle relaxants may be broadly classed into two types: centrally acting and locally acting. The exact mechanism of action of centrally acting muscle relaxants is not known, but may be due to central nervous system depression.

There are a number of known centrally acting muscle relaxants, including phenylglyceryl ether and its derivatives, including methocarbamol. Methocarbamol has no direct action on the contractile mechanism or the non-contractile functions of striated muscle (including metabolic and thermogenic functions in the body), the motor end plate or the nerve fibre. It also has a sedative effect.

Guaifenesin (glyceryl guaiacolate) is also a centrally acting muscle relaxant that is believed to depress or block nerve impulse transmission at the internuncial neuron level of the subcortical areas of the brain, brain stem, and spinal cord. It also has mild analgesic and sedative actions.

Other known muscle relaxants include chlorphenesin, chlorphenesin carbamate, chlorzoxazone, carisoprodol, mephenesin, meprobamate, dantrolene, and 3-phenoxy-1,2-propanediol.

Pharmaceutically acceptable salts of known muscle relaxants may also be used in the compositions, methods and uses of the present invention.

Nitrosylated Phenylgyleryl Ethers

In the present invention, a single compound may be used. One such example is a compound of formula:

wherein:
R$^1$ is H, halo, C$_{1-6}$ alkoxy or C$_{1-6}$ alkyl;
R$^2$ is H, NO$_2$ or C(O)NH$_2$;
R$^3$ is H, NO$_2$ or C(O)NH$_2$; and
at least one of R$^2$ and R$^3$ is NO$_2$;
or a pharmaceutically acceptable salt of the compound.

In an exemplary invention embodiment, R$^1$ is in the ortho position and is methyl or methoxy; or R$^1$ is in the para position and is chloro. In another exemplary embodiment, R$^1$ is hydrogen.

In a further exemplary embodiment, the compound is:

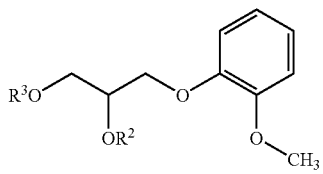

wherein:
R² is H, NO₂ or C(O)NH₂; R³ is H, NO₂ or C(O)NH₂; and at least one of R² and R³ is NO₂; or a pharmaceutically acceptable salt thereof.

In a further exemplary embodiment, the compound is:

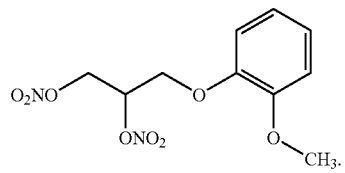

Formulations and Delivery Methods

The compounds and compositions of the present invention may be provided to precursor muscle cells by any suitable means, preferably directly (e.g., in vitro by addition to culture medium, or in animals in vivo locally by injection or topical administration at a treatment site) or systemically (e.g., parenterally or orally). Preferably, the compounds and compositions comprise part of a physiologically acceptable solution so that in addition to delivery of the desired agent to the target cells, the solution does not otherwise adversely affect the electrolyte and/or volume and/or metabolism of the cells or tissue or subject.

The pharmaceutical compositions and compounds as utilized in this invention can be administered by intranasal, oral, inhalational, enteral, topical, intrauterine, vaginal, sublingual, rectal, intramuscular, intrapleural, intraventricular, intraperitoneal, ophthalmic, intravenous, or subcutaneous means.

If desired, a given compound or composition may be adapted to different situations by association with a suitable molecule. For example, NO donors may be made more soluble or dispersible in physiological solutions than the corresponding original form.

It will be appreciated that the actual amounts of active compounds used will vary according to the specific compound being utilized, the particular compositions formulated, the mode of application, and the particular site of administration. Optimal administration rates for a given protocol of administration can be readily ascertained by those skilled in the art, using conventional dosage determination tests conducted with regard to the foregoing guide lines. See as a general guideline, Remington's Pharmaceutical Science, 16$^{th}$ Edition, Mack (Ed.), 1980.

According to the present invention, a "therapeutically effective amount" of a compound, combination or pharmaceutical composition of the invention is an amount which is sufficient to achieve the desired pharmacological effect. Generally, the dosage required to provide an effective amount of the composition, and which can be adjusted by one of ordinary skill in the art, will vary, depending upon the age, health, physical condition, sex, weight and extent of disease, of the recipient. Additionally, the dosage may be determined by the frequency of treatment and the nature and scope of the desired effect.

The compositions described herein may be administered as part of a sustained-release formulation (i.e., a formulation such as a capsule or resin or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane. Carriers for use within such formulations are biocompatible, and may also be biodegradable; preferably the formulation provides a relatively constant level of modulating agent release. The amount of modulating agent contained within a sustained-release formulation depends upon the site of implantation, the rate and expected duration of release and the nature of the condition to be treated or prevented.

It is noted that humans are generally treated longer than mice or other experimental animals exemplified herein. Accordingly, the length of the treatment generally may be proportional to the length or intensity or prior duration of the disease or pathophysiological process, and may further depend on the animal species, drug effectiveness and degree of effect required or recommended. The doses may be single doses or multiple doses over a period of one to several days or longer.

In one aspect, the pharmaceutical compositions and compounds of this invention are administered topically, especially when the target of treatment includes areas or organs readily accessible by topical application, including diseases of the eye, the skin, or the lower intestinal tract. Topical application may also be readily used to administer the combinations, compounds and compositions of the invention to tissue below the skin, such as muscle. Suitable topical formulations may be prepared for each of these areas or organs.

Topical application for the lower intestinal tract may be effected in a rectal suppository formulation or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

Formulations suitable for topical administration to the eye also include eye drops wherein the active ingredients were dissolved or suspended in a suitable carrier, especially an aqueous solvent for the active ingredients. The active ingredients were preferably present in such formulations in a concentration of 0.5 to 20%, advantageously 0.5 to 10% and particularly about 1.5% w/w.

One can use topical administration to deliver a compound of the invention by percutaneous passage of the drug into the systemic circulation of the patient. The skin sites include anatomic regions for transdermally administering the drug, such as the forearm, abdomen, chest, back, buttock, thigh and retroauricular area. The compound is administered to the skin by placing on the skin either a topical formulation comprising the compound or a transdermal drug delivery device that administers the compound. In either embodiment, the delivery vehicle is designed, shaped, sized, and adapted for easy placement and comfortable retention on the skin, or the formulation is applied directly on the skin in a prescribed amount and schedule.

Formulations suitable for topical administration include liquid or semi-liquid preparations suitable for penetration through the skin (e.g., liniments, lotions, ointments, creams, gels or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but not more than 5% w/w, or from 0.1% to 1% of the formulation.

When formulated in an ointment, the active ingredients may be employed with either paraffinic or a water-miscible ointment base. Alternatively, the active ingredients may be formulated in a cream with an emulsified cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include methocarbamol, longer-chain alcohols, dimethylsulfoxide and related analogs.

A variety of transdermal drug delivery devices can be employed with the compounds of this invention. For example, a simple adhesive patch comprising a backing material and an acrylate adhesive can be prepared. The drug and any penetration enhancer can be formulated into the adhesive casting solution. The adhesive casting solution can be cast directly onto the backing material or can be applied to the skin to form an adherent coating.

Transdermal administration may be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In other embodiments, the compound of the invention will be delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir.

Matrix patches comprising a backing, a drug/penetration enhancer matrix, a membrane, and an adhesive can also be employed to deliver a compound of the invention transdermally. The matrix material typically will comprise a polyurethane foam. The drug, any enhancers, vehicles, stabilizers, and the like are combined with the foam precursors. The foam is allowed to cure to produce a tacky, elastomeric matrix which can be directly affixed to the backing material.

Also included within the invention are preparations for topical application to the skin comprising a compound of the invention, typically in concentrations in the range from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, flavouring agents, colouring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, flavouring agents, colouring agents, and the like.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween™ 60, Span™ 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

The topical pharmaceutical compositions according to this invention may also include one or more preservatives or bacteriostatic agents, e.g., methyl hydroxybenzoate, propyl hydroxybenzoate, chlorocreosol, benzalkonium chlorides, and the like. The topical pharmaceutical compositions also can contain other active ingredients such as antimicrobial agents, particularly antibiotics, anesthetics, analgesics, and antipruritic agents, as well as anti-fungal agents. Perfumes or volatile agents that confer an odour on the composition while, by evaporating, they 'set' or dry a topical formulation/application, may also be included.

The compounds of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora Transmucosal drug dosage forms (e.g., tablet, suppository, ointment, pessary, membrane, and powder) are typically held in contact with the mucosal membrane and disintegrate and/or dissolve rapidly to allow immediate systemic absorption.

Muscle Conditions

The NO-related treatments of the present invention may be used for any condition where regeneration or growth, or the regulation of regeneration or growth processes, of muscle is desired.

In one embodiment, the invention may be used as part of pre- or post-surgical procedures, to promote, encourage or allow optimal or efficient repair of muscle damage by muscle regeneration rather than formation of scar tissue and fibrosis.

The invention may be used to form muscle tissue in culture (i.e., in vitro) during bio-engineering, for later use in transplantation; e.g. to replace diseased or surgically or traumatically removed muscle, or in the treatment of burn injuries.

In another embodiment, the invention may be used as part of rehabilitation procedures by stimulating muscle formation and/or growth, and thereby increasing muscle function after muscle disuse or wasting, e.g. after bedrest or confinement, stroke or coma-induced incapacitation, arthritis, casting, peripheral nerve section and regrafting of muscle or nerve or neurovascular-muscle transplantation between subjects or re-location in one subject) and in anticipation of a requirement to prevent permanent or severe atrophy using rehabilitation strategies in anticipation of secondary or curative surgical or medical/pharmacologic treatment.

The NO-related treatments of the present invention are useful particularly in the treatment of diseases and conditions in which muscle disease-specific processes frustrate or interfere with muscle regeneration (e.g., genetic mutations of pathways involving the genes for muscle regulatory proteins such as MyoD, myf5, myogenin, MRF4; other proteins that modulate myogenesis including NOS (the activity of which produces NO) and other molecules in the dystrophin-associated protein complex that interact and affect NOS expression, localization or signaling), cell proliferation, collagen breakdown or formation in muscle repair, matrix and membrane proteins in muscle; growth factors such as basic fibroblast growth factor, hepatocyte growth factor/scatter factor, insulin-like growth factors, insulin, and their relevant receptors).

The NO-related treatments of the present invention may also be useful in treating smooth muscle and cardiac muscle cell growth, dysfunction, injury, infarction etc., and in conditions such as those characterized by muscle fiber instability or rigidity or loss of or excessive adhesion between the satellite cell and the fiber. These include conditions originating from genetic mutation or toxic exposure or ischemia-reperfusion injury. As an example, important linkages may be weakened a) between the fiber cytoskeleton, sarcolemma, integrins, and extracellular matrix/external lamina, b) between the sarcolemma, M-cadherins and other adhesion proteins and satellite cells, c) between fusing muscle precursors, d) between extracellular matrix and growth factors, and e) between enzymes/proteins and extracellular matrix or sarcolemma.

Specifically, NO-related treatments of the present invention are useful for regenerating damaged muscle tissue, in normal muscle such as after injury or traumatic or therapeutic loss of muscle, and in particular in dystrophic muscles such as Duchenne, Becker, Emery-Dreifuss, Landouzy-Dejerine, Scapulohumeral of Seitz, Limb-girdle (Erb and other types), von Graefe-Fuchs, Oculopharyngeal, Myotonic (Steinert) and Congenital dystrophies or any condition where atrophy and/or fiber loss or muscle wasting or toxicity or unchecked growth of adipose or fibrous connective tissue in a damaged, infected or diseased muscle or any age-related muscle conditions are prevalent and contributory to decreased functional capacity of the muscle and/or of the human or animal.

In another embodiment, the NO-related treatment of the present invention can be used to increase muscle mass in normal muscle, e.g. during aging and athletic activity in humans or animal species (e.g. horse, dog). The manipulation of muscle precursor cell activation may be directed differentially to different muscles which are distinctly susceptible to various conditions such as injury, disease, functional demands, muscle-specific endurance training and individual use.

Practice of the invention will be more fully understood from the following examples, which are presented herein for illustration only and are not intended to limit the invention in any way.

EXAMPLES (A) Muscle Relaxant and No Donor Combined Therapy
(1) In Vitro Studies

The effect of NO donors ISDN and DPTA, and muscle relaxant methocarbamol (MC) on mouse EDL muscle cultures was tested.

(a) Normal Mice

Methods:

Extensor digitorum longus (EDL) muscles were dissected cleanly and carefully from normal C57Black/6 mice (8 weeks old) without stretching or trauma that could easily activate satellite cells. Each muscle was aligned radially in one well of a 6-well Flex II culture plate (Flexcell International, N.C., USA), and the tendons were pinned so the muscle was at resting length. The muscles were incubated in growth medium (Dulbecco's Minimum Essential Medium, DMEM, containing 15% v/v horse serum (HyClone Laboratories Inc.) and 2% v/v chick embryo extract (ICN Biomedicals) at 37° C. in 5% $CO_2$). Muscles in the wells were treated with or without an NO donor. [$^3$H]-Thymidine was added to the medium at the beginning of treatment, and cultures were maintained for 24 hours to allow incorporation of the isotope into new DNA. At the end of 24 hours, muscles were removed from wells, tendons were trimmed away, and the muscles were frozen at −20° C. for future analysis.

DNA was isolated from the tissues. DNA synthesis was assayed by scintillation counting in Ready Safe scintillation cocktail (Beckman), and the concentration of DNA in each sample was assayed using a fluorescence assay (calibrated against a standard curve). The data were calculated as DNA synthesis per microgram of DNA in each sample.

Figure 3:
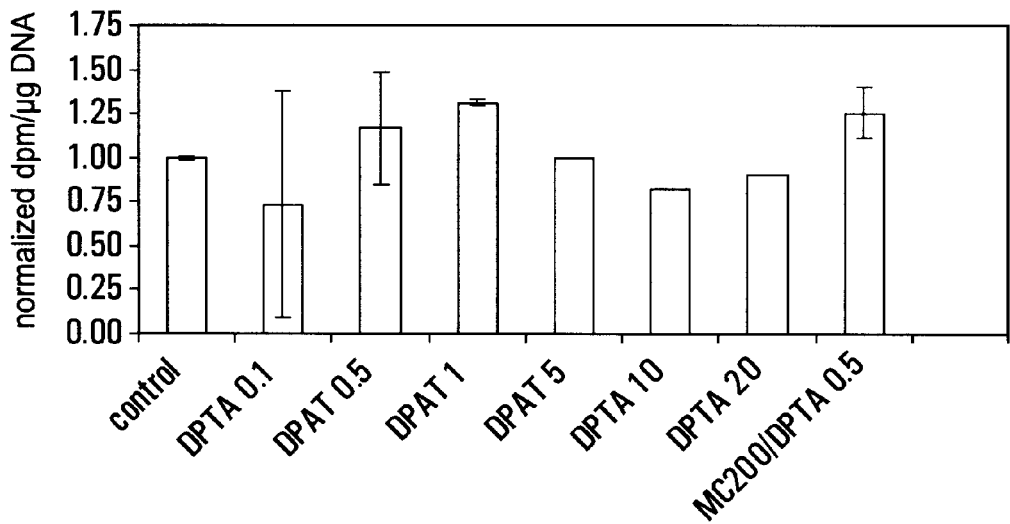
FIG. 3 is a graph showing the normalized results of experiments measuring the effect on DNA synthesis of ISDN alone and a combination of ISDN and methocarbamol on the cells in EDL muscles from C57Black/6 mice having normal muscle in a whole-muscle culture preparation.
Figure 4:
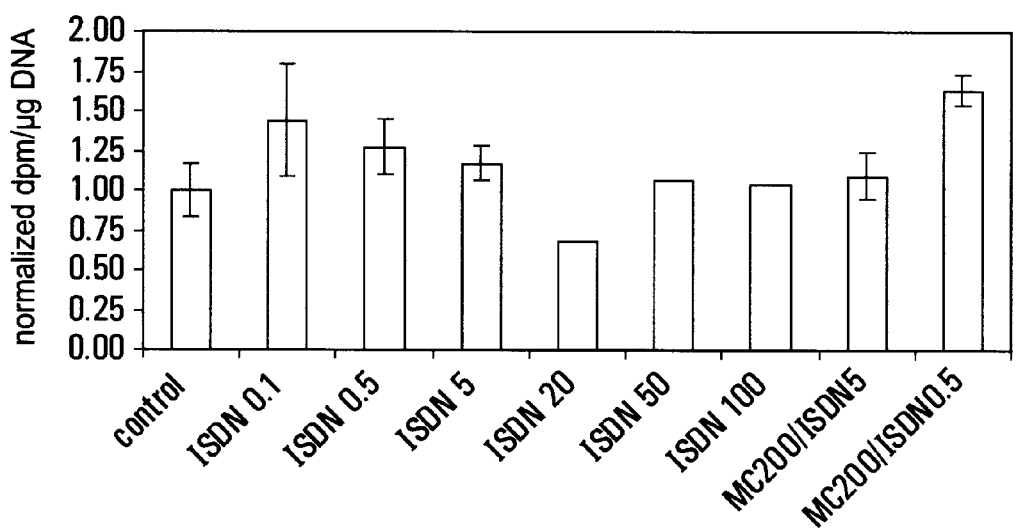
FIG. 4 is a graph showing the normalized results of experiments measuring the effect on DNA synthesis of DPTA alone and a combination of DPTA and methocarbamol on the cells in EDL muscles from normal C57Black/6 mice in a whole-muscle culture preparation.
Figure 5:
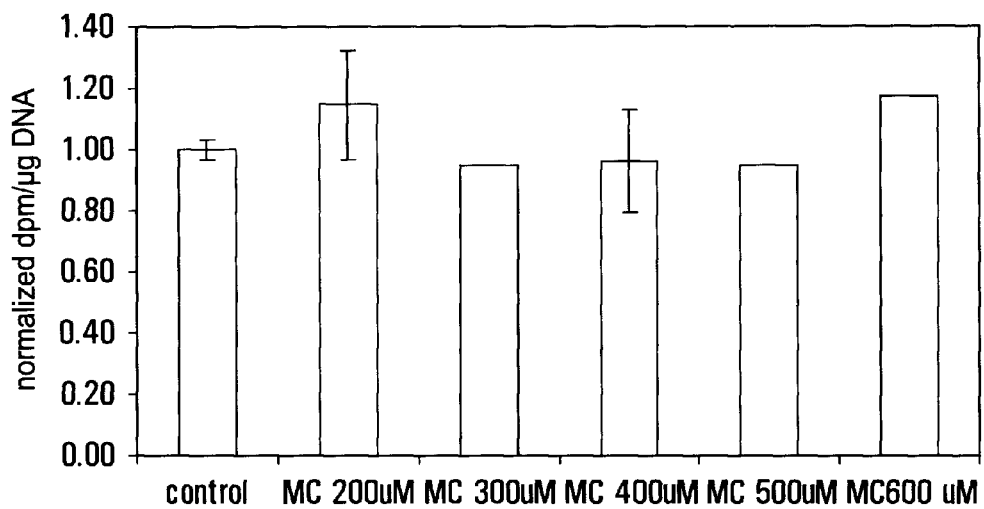
FIG. 5 is a graph showing the normalized results of experiments measuring the effect on DNA synthesis of methocarbamol alone on the cells in EDL muscles from normal C57Black/6 mice in a whole-muscle culture preparation.

Results:

The results of the DNA scintillation count are presented in FIGS. 3, 4 and 5, normalized to the control. FIGS. 3 and 4 show the results of three matched experiments and FIG. 5 shows the results of seven matched experiments, according to the above Methods. A comparison of the results in FIGS. 3 and 5 suggests that a combination of MC(200 µM)/ISDN(0.5 µM) increases DNA synthesis in EDL muscle culture over the use of the same amounts of MC and ISDN alone in cultures of EDL muscles from normal mice. Similarly, a comparison of FIGS. 4 and 5 suggests that the combination of MC(200 µM)/DPTA(0.5 µM) increases DNA synthesis in EDL muscle culture over the use of the same amount of either DPTA and MC alone, in cultures of EDL muscles from normal mice. Together, these results suggest that a combination of an effective amount of a muscle relaxant and an NO donor will increase muscle cell proliferation and thereby repair injured muscle.

(b) mdx Mice

Figure 6:
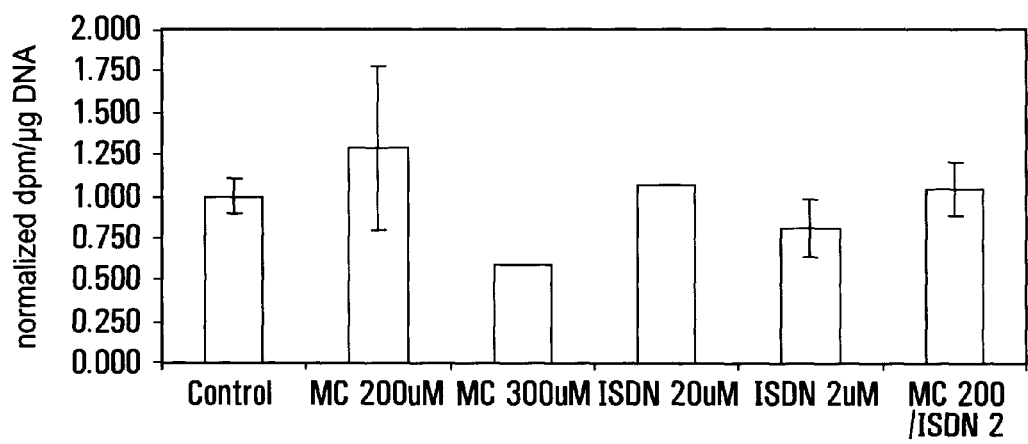
FIG. 6 is a graph showing the normalized results of experiments measuring the effect on DNA synthesis of ISDN alone and a combination of ISDN and methocarbamol on the cells of EDL muscles from mdx dystrophic mice in a whole-muscle culture preparation.

The experiment was twice repeated using mdx mice. The results of these further experiments are shown in FIG. 6. These results suggest that a combination of a muscle relaxant, like methocarbamol, and a NO donor, like ISDN, may be an effective treatment in modulating satellite cell activation in dystrophic muscle.

(2) In Vivo Studies (a) Methocarbamol and ISDN

Four matched experiments were performed in which animals were treated by exposure to one of the following four ointments applied to the skin of the back:

1. Control (treated with an ointment base of sodium lauryl sulfate 1%, propylene glycol 12%, stearyl alcohol 25%, white petrolatum 25%, purified water 37% only),
2. MC (treated with base ointment containing 1% methocarbamol),
3. ISDN (treated with base ointment containing 0.2% isosorbide dinitrate, a nitric oxide donor), and
4. MC/ISDN (treated with base ointment containing both 1% methocarbamol and 0.2% isosorbide dinitrate).

In a pilot study, the control treatment (base cream only) was found to be equivalent to "no-treatment".

Methods:

Animals were housed singly in cages and randomly assigned to either control or treatment groups, all having access to distilled water and normal chow ad libitum. Due to the use of Elizabethan collars, food was made available to animals on the cage floor.

Ointments were applied according to the following procedure.

1. Animals were anesthetized with isoflurane and the mid-dorsal skin (on the back) was shaved, washed with soap and water, and air dried.
2. The ointment was applied to the sterile pad on an adhesive bandage. Control bandages were coated with the ointment base only. After topical application in which the bandages were applied to the shaved back region, bandages were wrapped with medical adhesive. The animals had the Elizabethan collar fitted while under anesthesia, to prevent their later chewing at the adhesive tape. Eyes were irrigated regularly, as animals were unable to groom well while wearing the cone.
3. Animals were treated for a total of 24 hours. There were no apparent effects of treatment on behaviour.
4. Two hours before euthanasia, the mice were injected with 2 µCi per gram body weight of tritiated-thymidine (intra peritoneal) to label DNA synthesis.
5. At 24 hours from the start of ointment application, animals were euthanized using cervical dislocation under anesthesia provided by pentobarbital injection. Tissues were collected by dissection and homogenized. DNA was isolated from the tissues. DNA synthesis was assayed by scintillation counting in Ready Safe scintillation cocktail (Beckman), and the concentration of DNA in each sample was assayed using a fluorescence assay (calibrated against a standard curve). The data were calculated as DNA synthesis per microgram of DNA in each sample.

Results:

Table 1 shows the results of the four experiments.

TABLE 1

| Tissue | Experiment | | | | Mean | Standard Error (SE) |
|---|---|---|---|---|---|---|
| | 1 | 2 | 3 | 4 | | |
| Back Muscle | | | | | | |
| Control | 423.5 | 394 | 320.1 | 301.76 | 359.8 | 29.1 |
| MC | 430.5 | 734* | 422.7 | 429.43 | 427.5 | 2.4 |
| ISDN | 517 | 377 | 400.7 | 375.03 | 417.3 | 33.6 |
| MC/ISDN (a) | 631 | 467 | 314.5 | 348.88 | 429.8 | 46.4 |
| MC/ISDN (b) | | 799* | 441.3 | 376.25 | | |
| Quadriceps | | | | | | |
| Control | 489.5 | 481 | 311.6 | 312.54 | 398.7 | 50.0 |
| MC | 507 | 573 | 404.1 | 340.9 | 456.3 | 51.8 |
| ISDN | 524 | 501 | 427.9 | 351.89 | 451.2 | 38.9 |
| MC/ISDN (a) | 714 | 573 | 412 | 347.31 | 485.7 | 51.1 |
| MC/ISDN (b) | | 609 | 374.6 | 369.87 | | |
| Heart | | | | | | |
| Control | | 199 | 128.6 | 199.96 | 175.9 | 20.5 |
| MC | | 186 | 221.3 | 240.76 | 216.0 | 13.9 |
| ISDN | | 214 | 168.7 | 222.86 | 201.9 | 14.5 |
| MC/ISDN (a) | | 153 | 159.1 | 225.68 | 206.0 | 14.3 |
| MC/ISDN (b) | | 254 | 219.9 | 224.46 | | |
| Gut | | | | | | |
| Control | | 175 | 170.2 | 139.56 | 161.6 | 9.6 |
| MC | | 123 | 239.2 | 225.9 | 196.0 | 31.8 |
| ISDN | | 160 | 141.4 | 218.86 | 173.4 | 20.2 |
| MC/ISDN (a) | | 134 | 139.8 | 185.91 | 178.1 | 13.7 |
| MC/ISDN (b) | | 169 | 235.3 | 204.45 | | |

(a) and (b): muscle samples were prepared from left and right representations of each skeletal muscle (back and quadriceps) and two samples of each of the heart and gut were typically used in the assays of DNA synthesis from each treated animal.
*Outlier data points, excluded from mean and standard error calculations.

Figure 7:
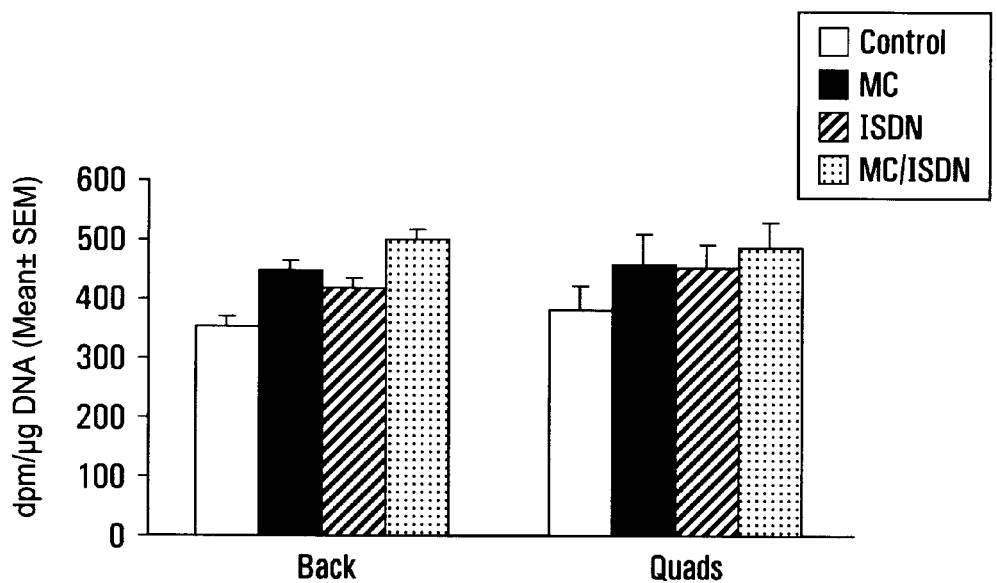
FIG. 7 is a graph of results of experiments comparing the increase in DNA synthesis in back muscle and quadriceps of normal C57Black/6 mice following topical application of a control (placebo), the muscle relaxant methocarbamol alone, the NO donor ISDN alone and a combination of methocarbamol and ISDN.

The mean results for the back muscles and quadriceps are plotted in FIG. 7. FIG. 7 shows that there was an increase in DNA synthesis in the back muscle during treatment with MC, ISDN and MC/ISDN, with the effects of treatment with the combination of MC/ISDN being greater than the individual effects of MC and ISDN alone. This result suggests that the cream formulation stimulated direct proliferation of muscle cells by topical application.

FIG. 7 also shows that there was a smaller increase in DNA synthesis in another muscle (here quadriceps), particularly with the treatment by combined MC/ISDN. This result suggests that there is a smaller but significant systemic effect to increase muscle cell proliferation in a normal animal.

As anticipated, heart muscle (not shown in FIG. 7), as a muscle that is non-proliferative while containing other tissues that can proliferate (blood vessels, lymphatics, endothelial tissue), served as the negative control and did not show a strong response to treatment. Gut (not shown in FIG. 7)

served as a positive control, since that epithelium is always proliferative. Isotopic labeling of DNA synthesis in the gut confirms that the isotope was available for uptake from the circulation and that differences in DNA synthesis are related to treatment and not to lack of uptake into the circulation.

In short, the MC/ISDN combination had a statistically significant effect on muscles directly underlying the area of cream application. The data suggests satellite cell activation and the promotion of their proliferation after a relatively short exposure (24 hours). This effect in a therapy could therefore directly promote the repair of injured normal muscle. There was a smaller activation/proliferation effect on the quadriceps muscle, presumably through absorption into the bloodstream and action of the NO at a distance from the area of application. Without being bound by any theory, this may be a result of direct NO action or from NO break down products. Alternatively, this may also be a result of nervous system signaling relayed via afferent nerves from the back muscle to the central nervous system (spinal cord or higher levels) and thence relayed to the other muscles, or by secondary release of, for example, hepatocyte growth factor (HGF) from the directly-exposed muscle which traveled through the circulation to the other muscles.

(b) Carisoprodol and DETA

Figure 8:
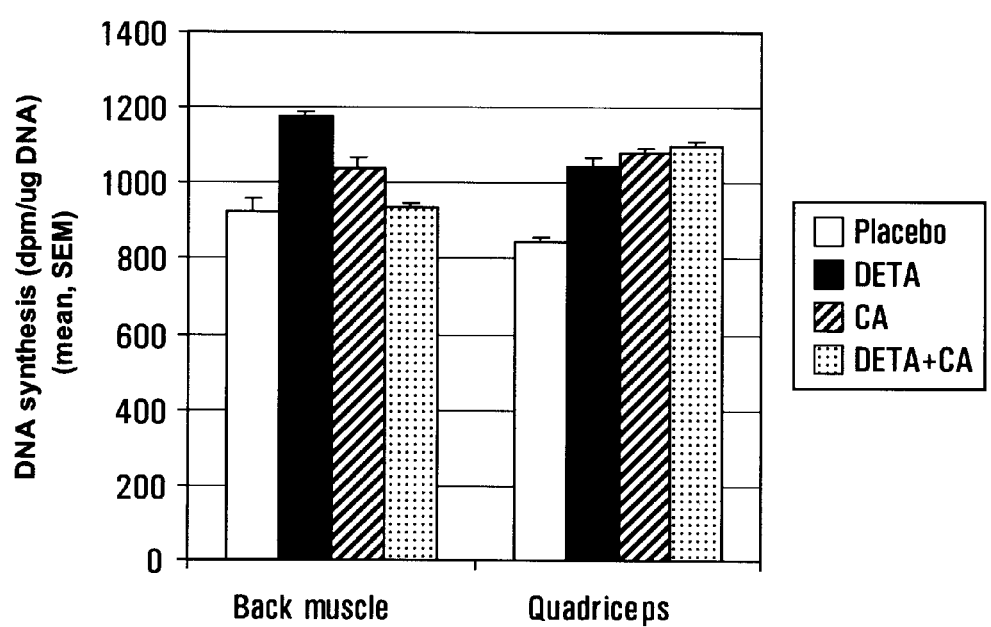
FIG. 8 is a graph of results of experiments comparing the increase in DNA synthesis in back muscle and quadriceps of normal C57Black/6 mice following topical application of a control (placebo), the muscle relaxant carisoprodol alone, the NO donor diethylenetriamine-NONOate (DETA) alone and a combination of carisoprodol and DETA.

The experiment was repeated using 0.25% carisoprodol (CA) and 1% diethylenetriamine-NONOate (DETA; Sigma), alone and in combination. Eight matched experiments were performed, and the results of these tests are shown in FIG. 8.

These experiments show that a muscle relaxant (carisoprodol) and an NO donor (DETA) both induce increased DNA synthesis in back and quadriceps muscles. The effect of the NO donor DETA is somewhat larger in the back muscle than the quadriceps, possibly as the muscle would be exposed to both a direct topical effect and a systemic effect. As well, different muscles likely have different dose-response characteristics for a given treatment, different numbers of satellite precursor cells as a proportion of non-satellite cell nuclei in the tissue, and different basal levels of DNA synthesis, each of which may affect the relative change in DNA synthesis in different muscles following treatment.

These results show only a small increase in DNA synthesis in the back muscle on use of the combination of carisoprodol and DETA over the control, and do not show an increase over the use of carisoprodol or DETA alone. But, the use of the combination of carisoprodol and DETA do show an increase in DNA synthesis in quadriceps over the control and over the use of the same amount of carisoprodol and DETA alone. The difference between the activity of the combination in the back muscle and quadriceps may be due in part to some toxicity, differential responses to the combination of topical and systemic exposure to the drug by the back muscle compared to the quadriceps that is exposed only through the systemic circulation, a different dose-response from the quadriceps, different numbers of satellite precursor cells as a proportion of non-satellite cell nuclei in the tissue, and different basal levels of DNA synthesis, which may affect the relative change in DNA synthesis in different muscles following treatment. As well, there may be a paradoxical effect such that the more potent treatment in the back muscle (compared to the quadriceps exposed to systemic treatment alone) may be reducing the effect in the back muscle relative to quadriceps as the dose-response curve exceeds the peak dose-response and begins to decline. There may also be a difference in sensitivity to the activating agents of the combination in the quadriceps and back muscle.

In view of the increase in DNA synthesis, these results also support a combination therapy of muscle relaxant and NO donor for repairing injured normal muscle.

(C) Nitrosylated Phenylglyceryl Ethers: Myonovin™

(1) Preparation of 1,2-di-O-nitro-3(o-methoxyphenoxy)-propanediol (MyoNovin™)

The compound:

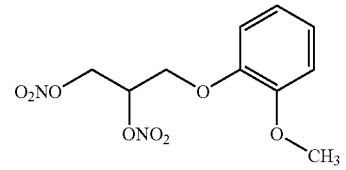

1, 2-di-O-nitro-3(o-methoxyphenoxy)-propanediol was prepared according to the following procedure.

Guaifenesin (1.982 g, 10 mmol) was suspended in tetrahydrofuran (THF) (50 ml) and silver nitrate ($AgNO_3$) (6.8 g, 40 mmol) was added all at once. After dropwise addition of freshly distilled thionyl chloride $SOCl_2$ (d=1.631; 2.38 g, 20 mmol, 1.46 ml) in ice-cold conditions, the mixture was stirred for 14 hours at room temperature. Pure water ($H_2O$) (25 ml) was added to the reaction system and the mixture was extracted with acetyl-acetate (AcOEt) (20 ml×3). The combined organic layers were washed with saturated sodium bicarbonate ($NaHCO_3$) (10 ml×3), then with distilled water (10 ml×3). The extract was dried with anhydrous magnesium sulphate ($MgSO_4$). The solvent was evaporated and the product was dried with silica gel using a Rotary Evaporator. The product was purified by silica gel (Aldrich #227196, Merck grade 9385, 230-400 mesh, 60A) column chromatography.

This procedure may be depicted as:

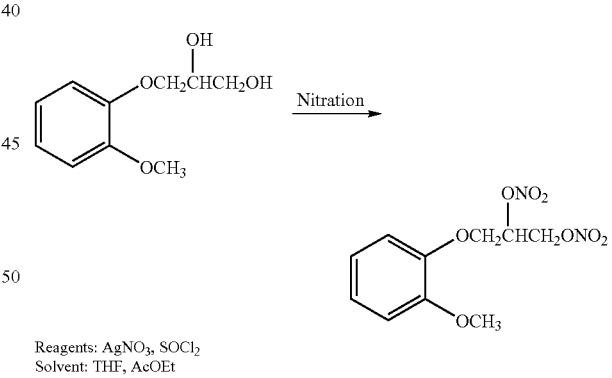

Reagents: $AgNO_3$, $SOCl_2$
Solvent: THF, AcOEt

Flash Chromatography:

A chromatography column (Kontes 30×500 mm) was packed with silica gel to 350 mm length and equilibrated with acetyl-acetate/hexane mixture (AcOEt/Hexane) (1:3, volume-to-volume). The separation and elution were performed with a slight air pressure on the top of the same solvents (AcOEt/Hexane at ratio of ⅓); the elution rate was controlled at one drop per second. Forty fractions were collected from the column at 25 ml per fraction following elution of the first 200 ml. In each fraction, bands were identified using fluorescent thin layer chromatography to examining the eluted compounds.

Figure 9:
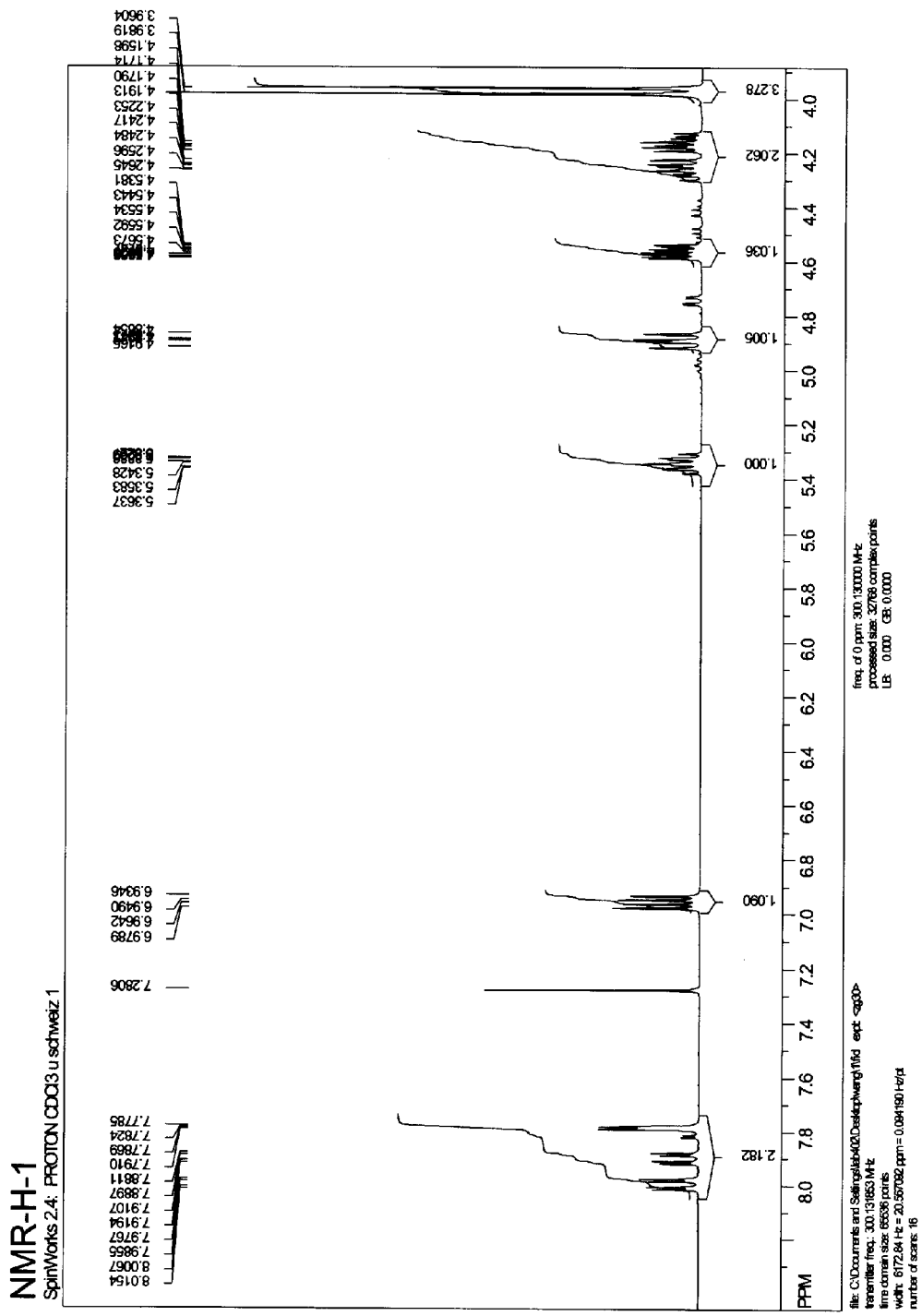
FIG. 9 is a $^1H$ NMR (nuclear magnetic resonance) spectrum of a compound of the invention.
Figure 10:
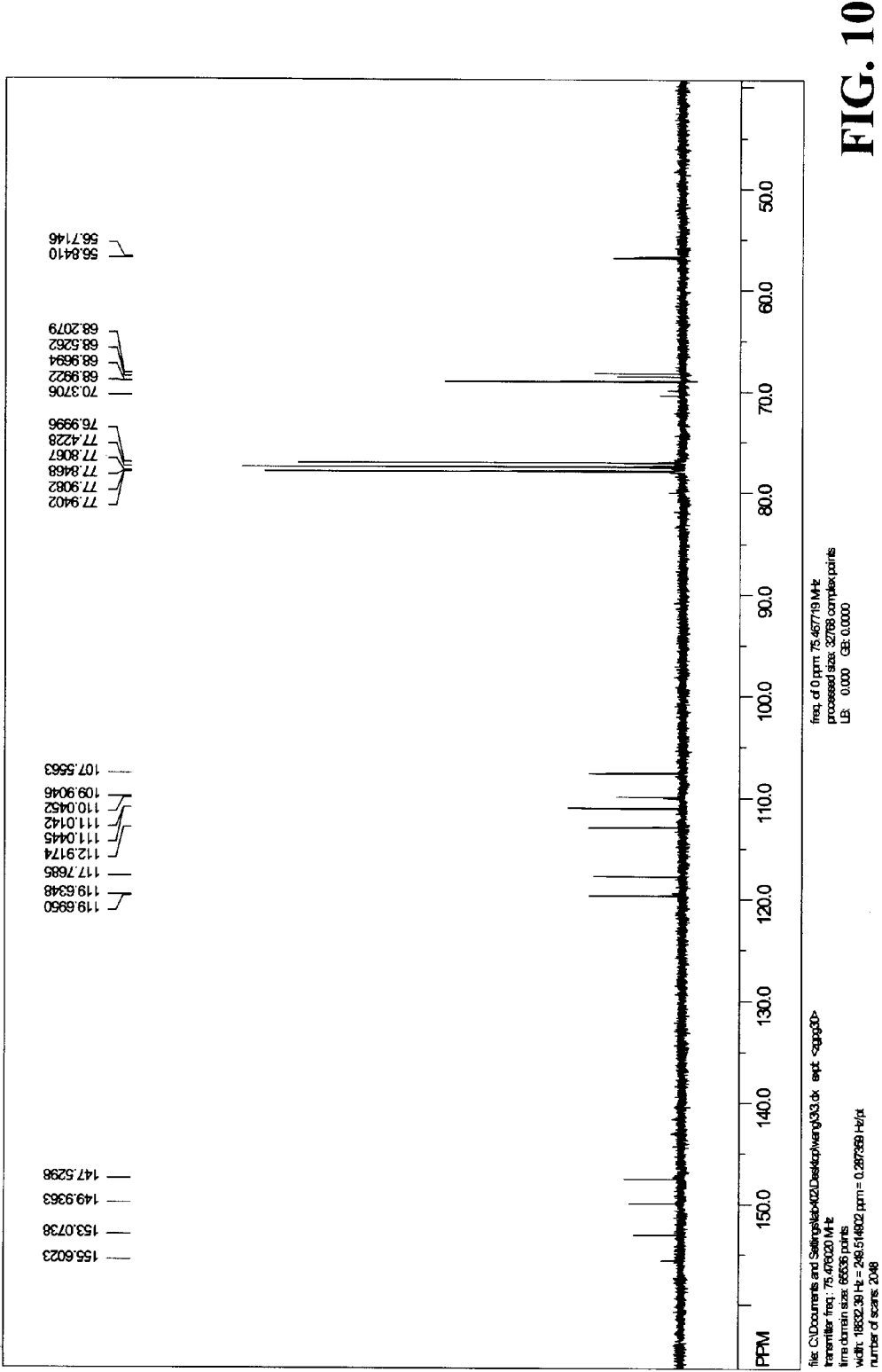
FIG. 10 is a $^{13}C$ NMR spectrum of the compound of FIG. 9.
Figure 11:
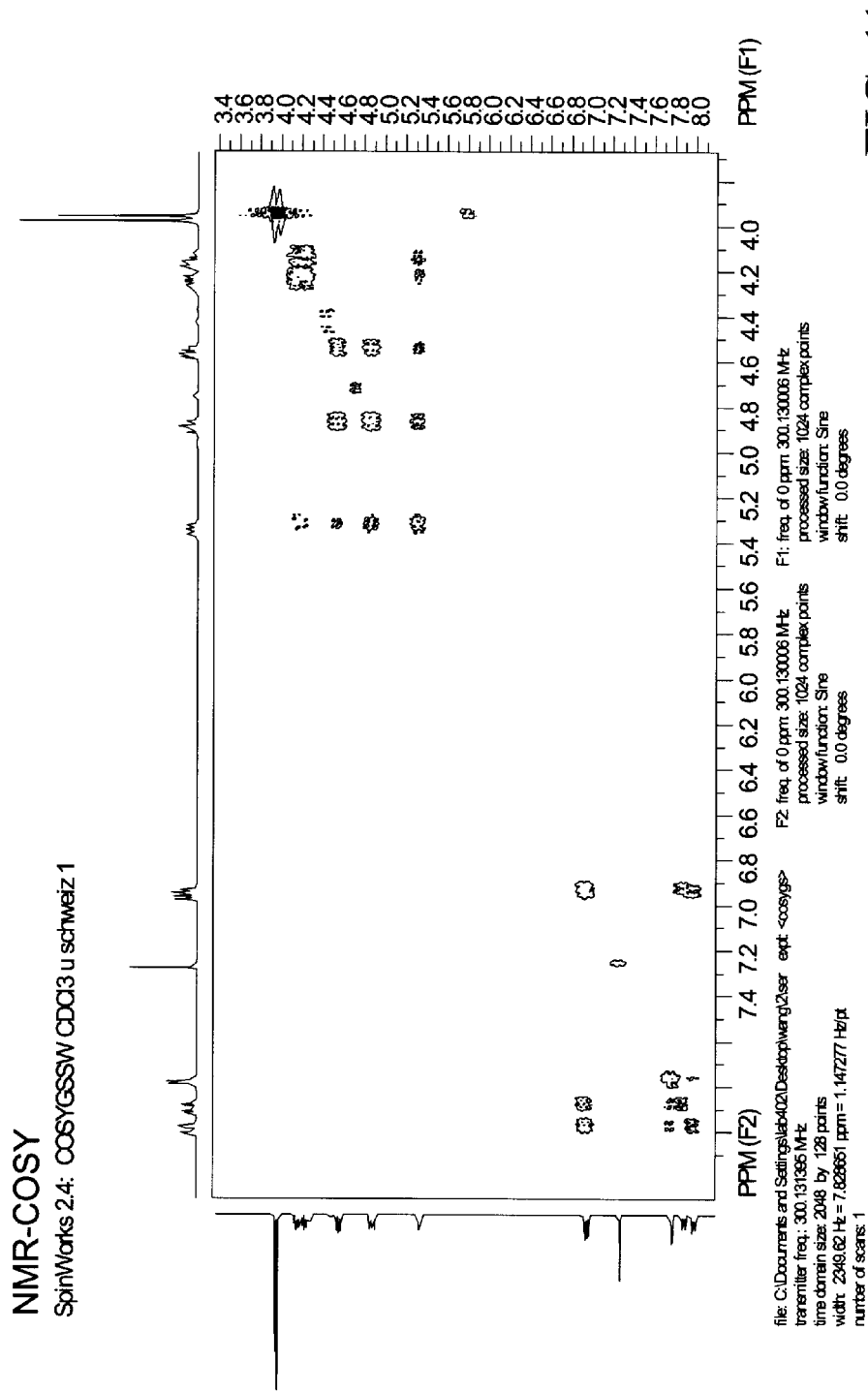
FIG. 11 is a NMR-COSY (Correlation SpectroscopY) spectrum used to assign the peaks of FIG. 9.
Figure 12:
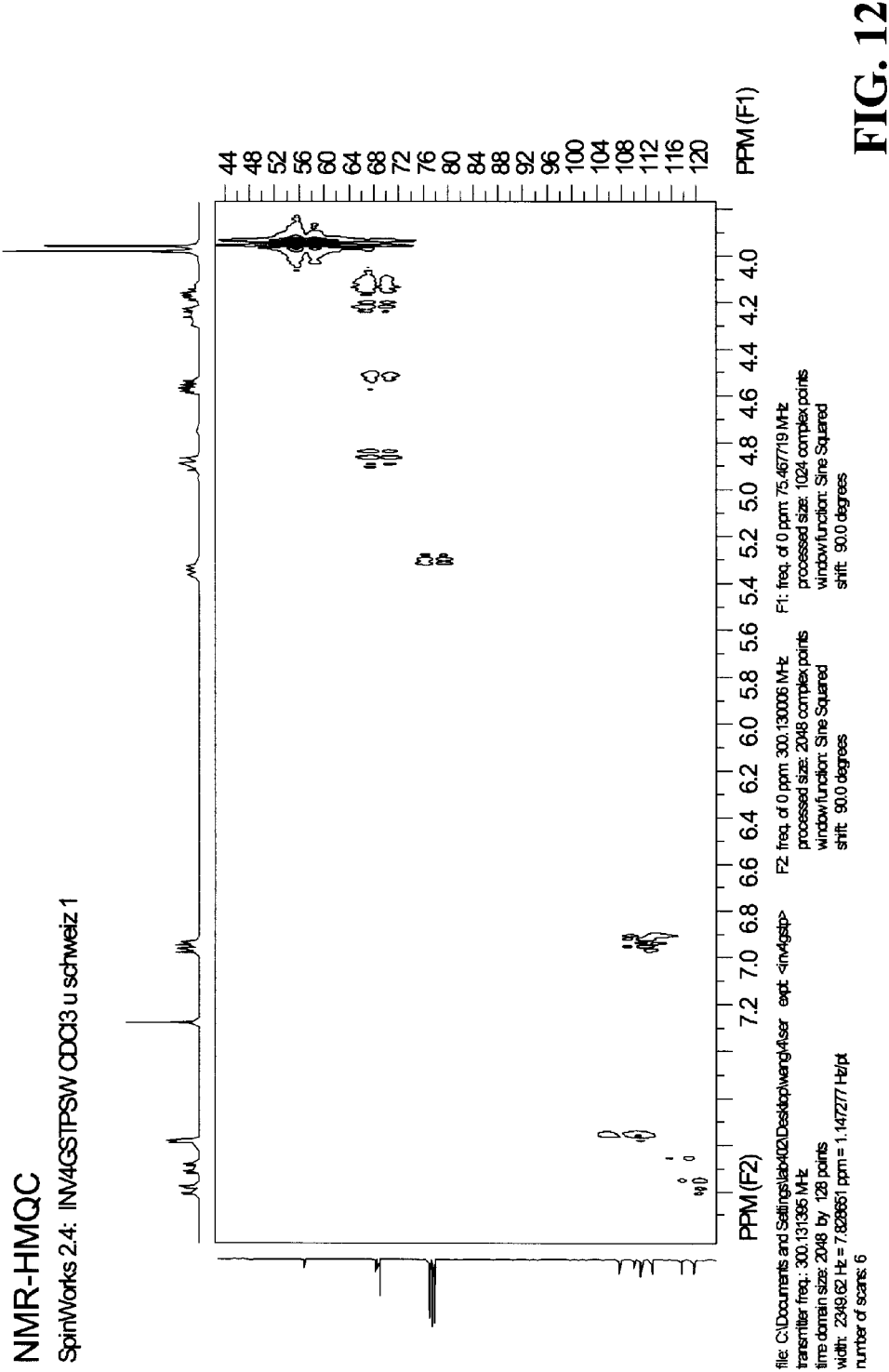
FIG. 12 is a NMR-HMQC (Heteronuclear Multiple Quantum Correlation) spectrum used to assign the peaks of FIG. 10.
Figure 13:
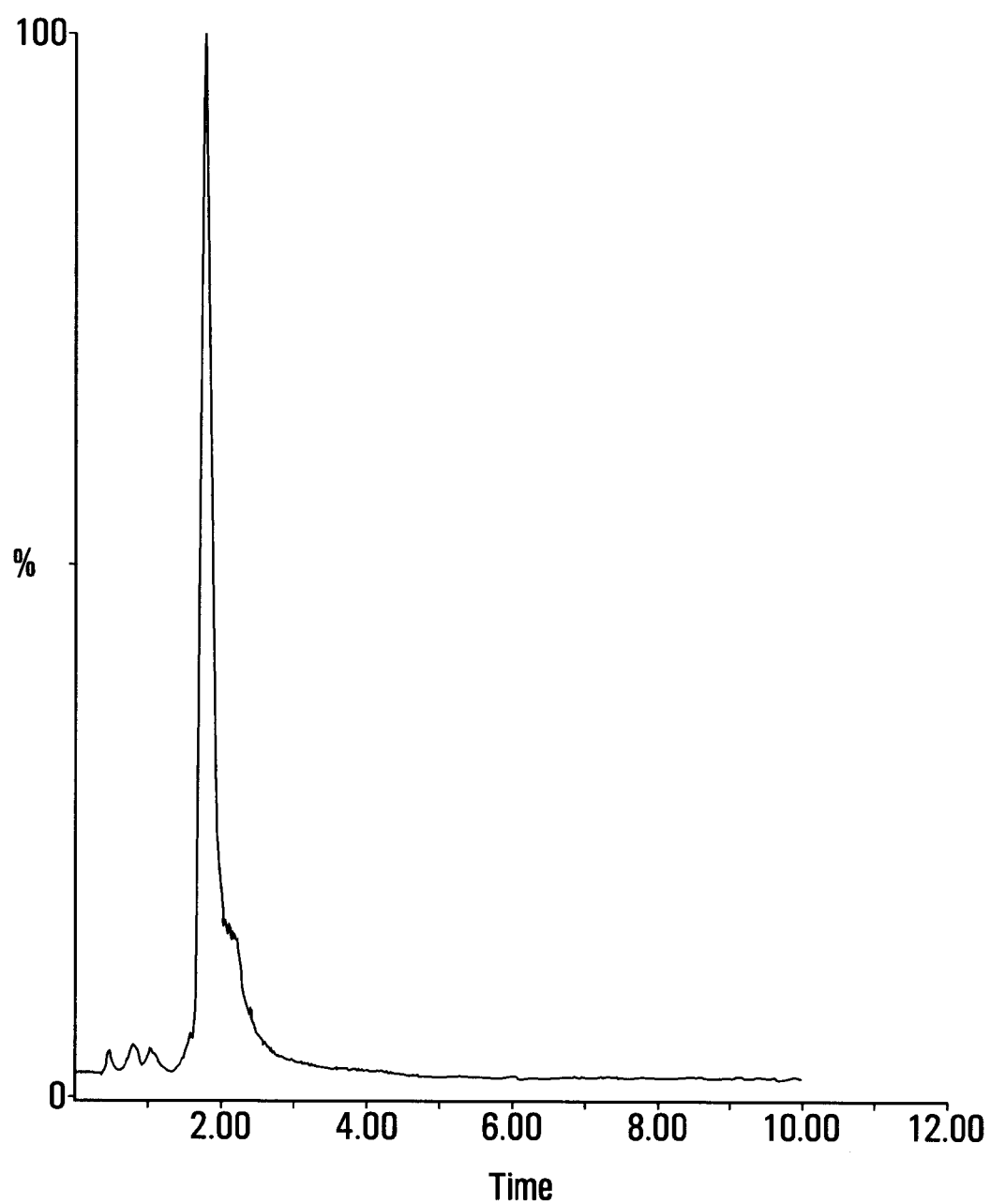
FIG. 13 is an HPLC (High Performance Liquid Chromatography) spectrum of the compound of FIG. 9.
Figure 14:
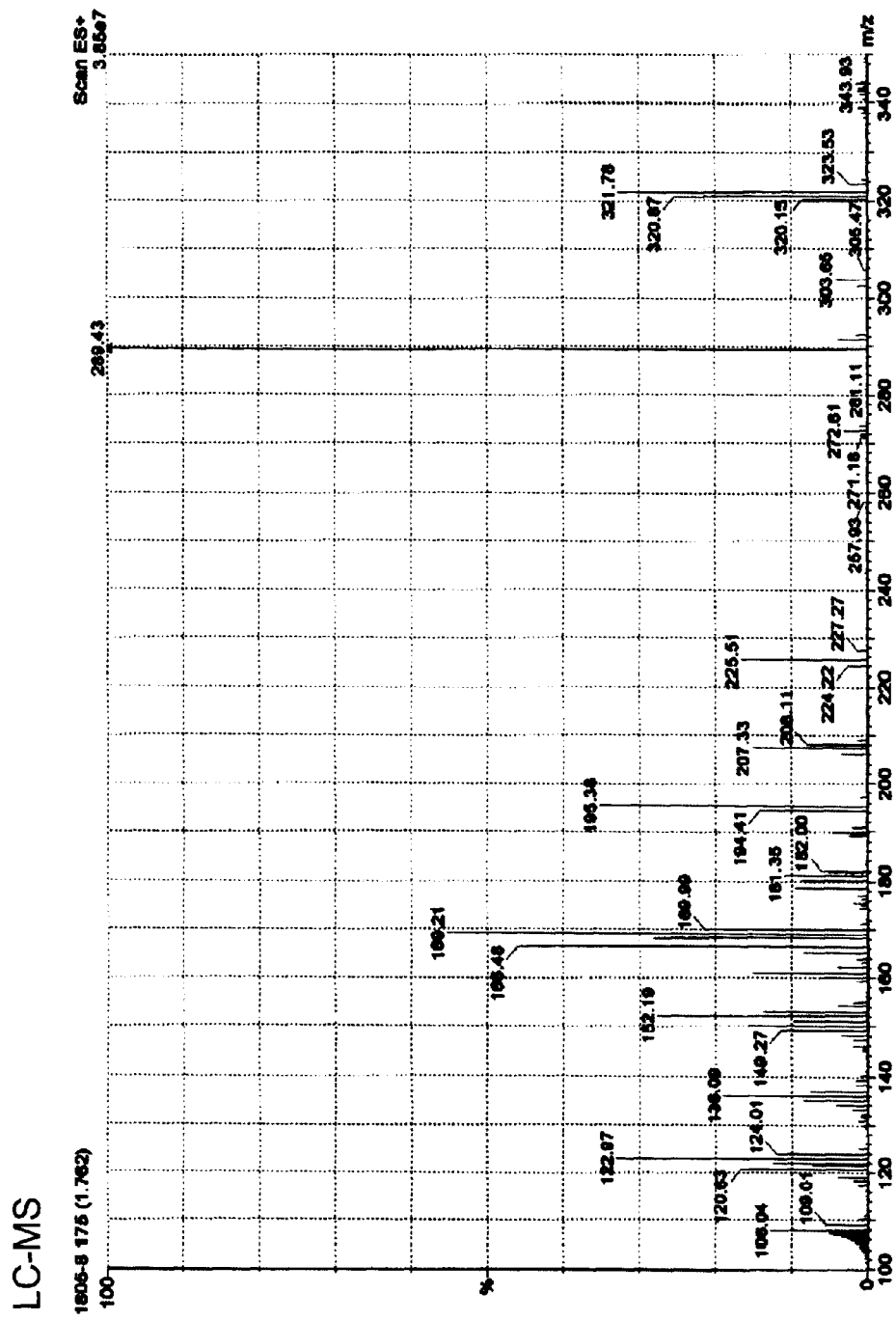
FIG. 14 is a LC-MS (Liquid Chromatography-Mass Spectrometry) spectrum of the compound of FIG. 9.
Figure 15A:
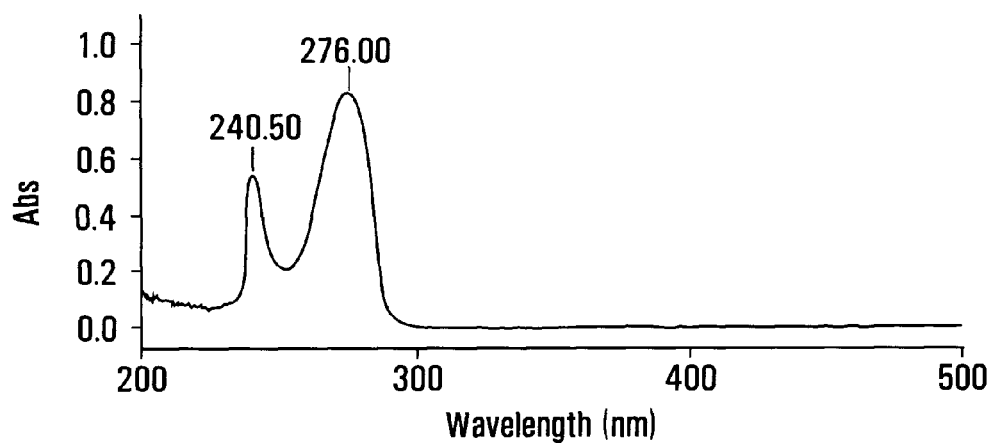
FIG. 15(a) is an IR spectrum of guaifenesin.
Figure 15B:
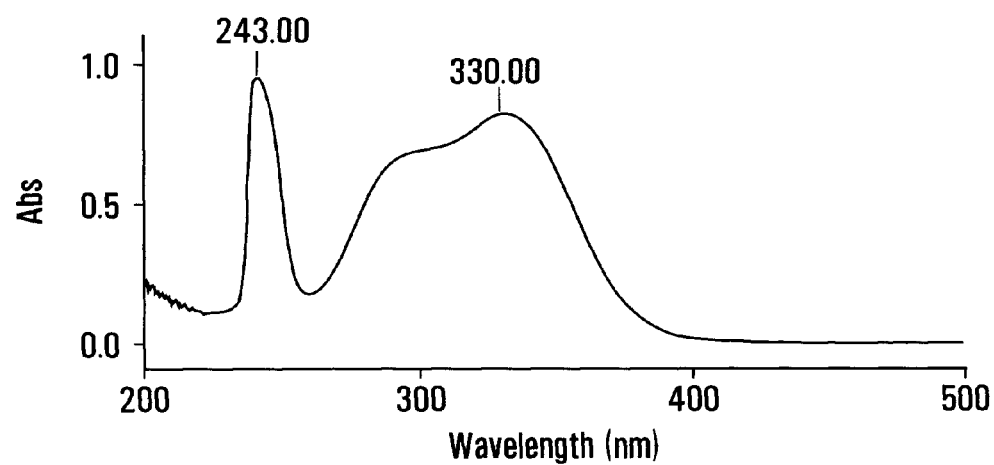
FIG. 15(b) is an IR (Infrared) spectrum of the compound of FIG. 9.
Figure 16:
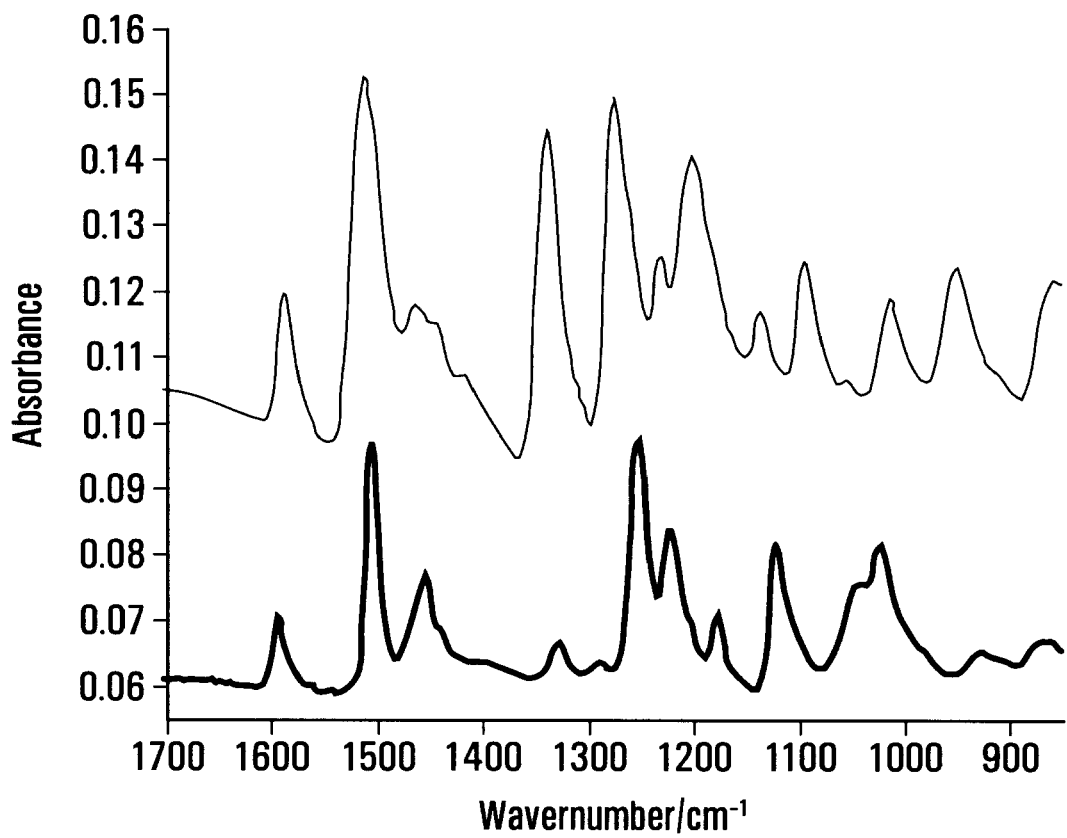
FIG. 16 is an UV (Ultra-Violet) spectrum of guaifenesin and the compound of FIG. 9.

The compound was identified using the following techniques:
1) The compound was characterized by $^1$H NMR (FIG. 9) and $^{13}$C NMR (FIG. 10). The NMR peaks were assigned by NMR-COSY (COrrelation SpectroscopY, a 2-dimensional H—H correlation NMR technique; FIG. 11) and NMR-HMQC (Heteronuclear Multiple Quantum Correlation spectroscopy, a 2-dimensional C—H correlation NMR technique; FIG. 12),
2) HPLC and LC-MS were used to obtain the molecular mass of the compound (FIGS. 13 and 14),
3) Ultraviolet spectrophotometry (FIG. 15b), together with a comparison with guaifenesin (FIG. 15a), and
4) Infrared spectrophotometry together with a comparison with guaifenesin (FIG. 16). MyoNovin is the upper tracing, and guaifenesin the lower.

The target compound has a molecular mass of 288.0675 g/mole and is identified as 1-(2,3-bis-nitrooxy-propoxy)-2-methoxy-benzene or 1,2-di-O-nitro-3(o-methoxyphenoxy)-propanediol. We have named it 'MyoNovin'.

(2) Testing of MyoNovin (a) Normal Mice

Figure 17:
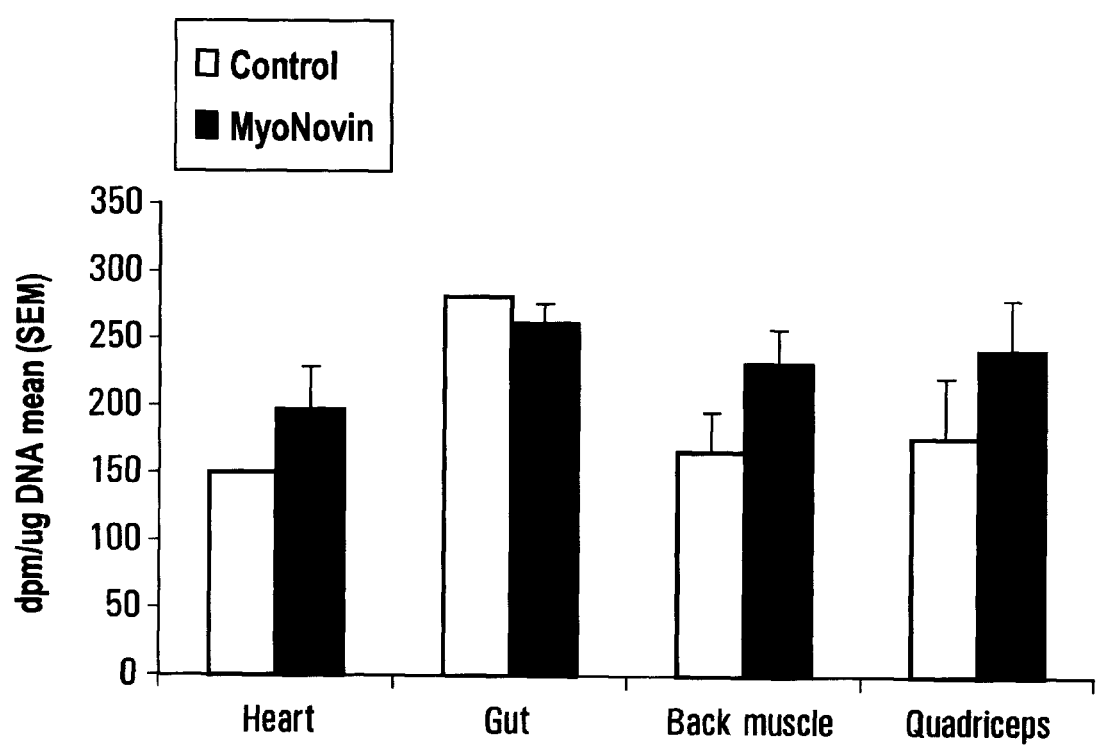
FIG. 17 is a graph of results of experiments comparing the increase in DNA synthesis in back muscle and quadriceps of normal C57 Black/6 mice following topical application of a compound of the invention and a control with gut and heart tissue functioning as a positive and negative control respectively.

MyoNovin was tested in vivo in animal experiments with the same transdermal approach as described for methocarbamol and ISDN. Six matched experiments were performed using MyoNovin, and six with ointment base alone. The results of these experiments are presented in FIG. 17.

Experiments on animals revealed the positive effects of treatment with the new compound, which stimulated 37-39% increase in muscle cell proliferation (DNA synthesis) over a 24-hour period, with no apparent side effects to animal behaviour, appearance or weight. The heart and gut once again functioned as a negative and positive control, respectively.

(b) mdx Mice

Figure 18:
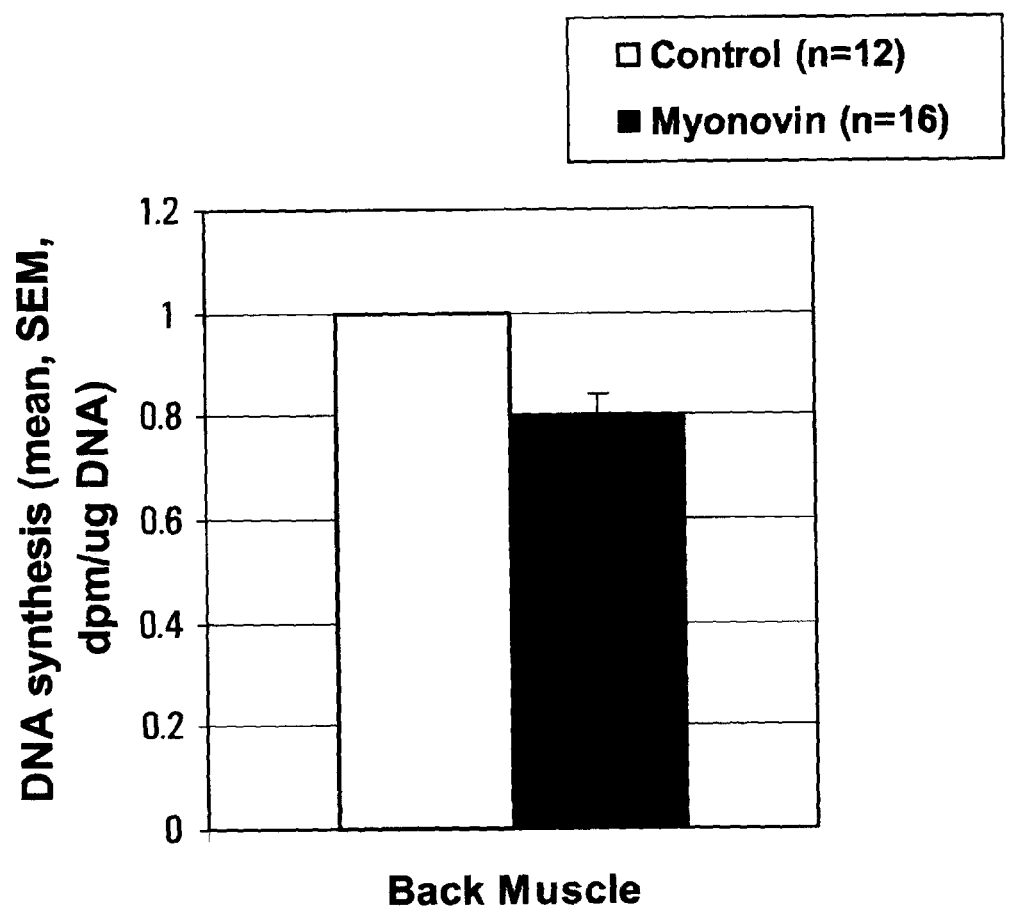
FIG. 18 is a graph showing the normalized results (relative to control) of experiments measuring change in DNA synthesis in back muscle of mdx dystrophic mice after topical application of a compound of the invention.

MyoNovin was also tested using the same transdermal approach as described above. The results normalized to the control are presented in FIG. 18. DNA synthesis was decreased following treatment by MyoNovin in back muscle compared to the control. This suggests a mediation of satellite cell activation in dystrophic muscle.

(c) Effect of Aging

Figure 19:
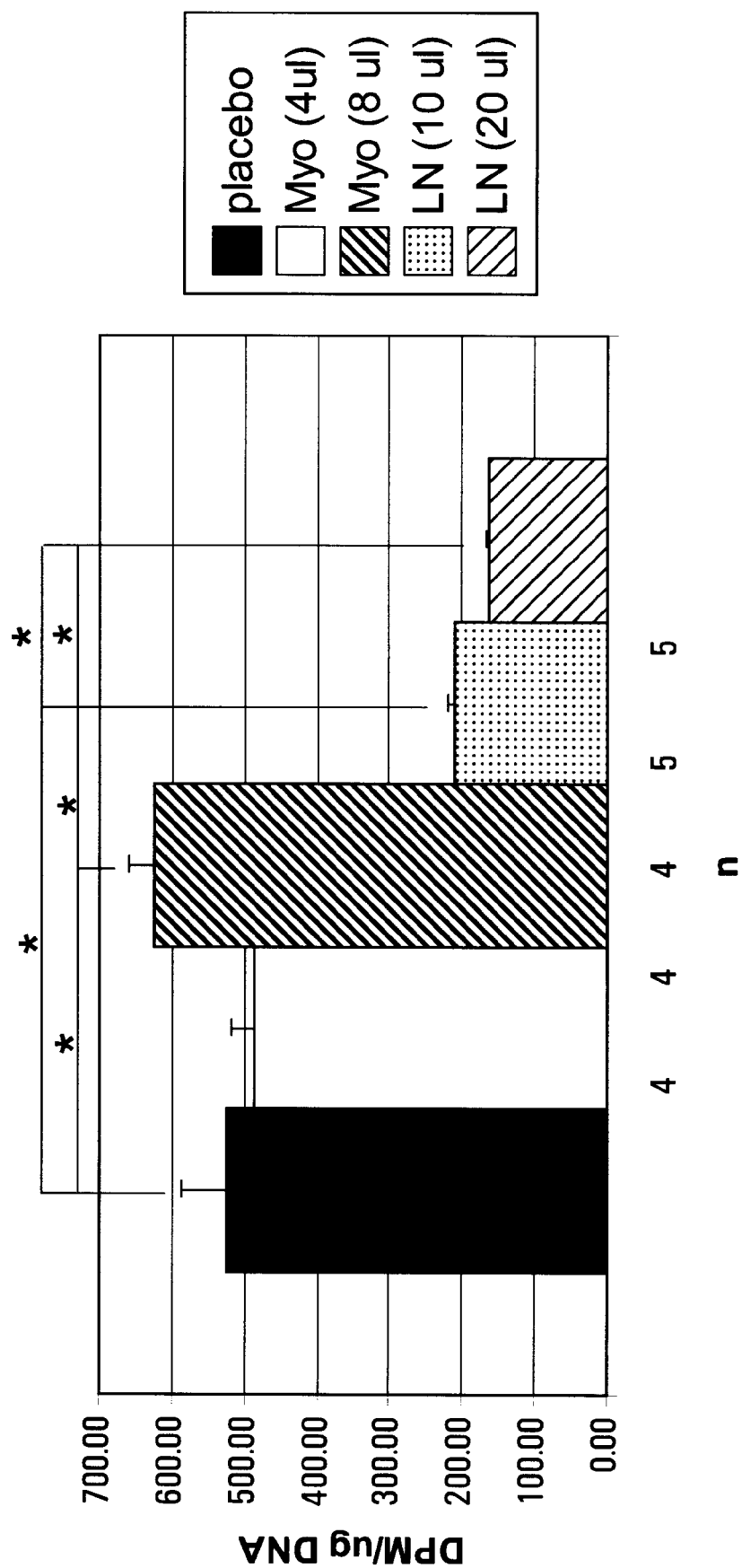
FIG. 19 is a graph showing the results of experiments measuring the effect on DNA synthesis of a control, a compound of the invention and the nitric oxide synthase (NOS) inhibitor L-nitro-arginine methyl ester (L-NAME) on the cells of EDL muscles harvested from 12 month old C57Black/6 mice and examined using a whole-muscle culture preparation.

Data from an experiment on EDL muscles in culture, isolated from old (12-month-old) normal C56BL/6 mice were conducted using the method described above for methocarbomol and ISDN. The results are presented in FIG. 19.

In this experiment, muscles were treated with MyoNovin (2 doses) or the NOS inhibitor, L-NAME (2 doses). Here the higher dose of MyoNovin induced increased DNA synthesis, as expected by the model (FIG. 1). Here both doses of L-NAME (very high) resulted in decreased DNA synthesis. These data suggest that satellite cells in old muscle can be stimulated to activate via MyoNovin, and that activation is very dependent on NO in the physiological range as modeled by FIG. 1, since the very strong NOS inhibition significantly reduced DNA synthesis. (The doses of L-NAME used here were very high compared to those used in developing the model of FIG. 1 to represent the satellite cell response to the physiological range of [NO]. The reduction may also be due, in part, to some toxicity, especially at the higher dose. The experiment also shows that isolated muscle in culture has similar response to MyoNovin as muscle in vivo (in living animals), and that the potential for using MyoNovin to treat muscle atrophy in aged muscle is significant.

(d) MyoNovin Induces NO Release

An Electron Paramagnetic Resonance (EPR) experiment was conducted to test whether MyoNovin induced NO release from tissue, and therefore whether the mechanism of action could be reasonably stated to be mediated via NO. The EPR spectra demonstrate that MyoNovin induced a strong release of nitric oxide from mouse tissue.

In the experiment liver and back muscle tissue taken from C57Black/6 mice were homogenized in ice-cold sucrose buffer. A small amount of MyoNovin was dissolved in dimethylsulfoxide and added to the tissue homogenates. An NO spin-trap molecule N-Methyl-D-glucamine dithiocarbamate (MGD) was added to the homogenate-MyoNovin mixture as a stable iron complex [10 µl of 50 mM MGD in saline; (containing MGD at 50 mM and $Fe^{2+}$ at 10 mM)] in order to trap any NO released from the tissue homogenate. The entire homogenate mixture plus NO spin-trap solution was then incubated for 1 hour at 37° C. After incubation, a sample of homogenate (16 µl) was loaded into a quartz capillary tube for determination of the EPR spectrum. EPR spectra were then obtained using a Bruker EMXEPR spectrometer (Bruker, Co., Billerica, Mass.) at room temperature (25° C.). The instrument settings were: 9.25 GHz microwave frequency; 100 kHz modulation frequency; 20 mW microwave power, 4 G modulation amplitude, 40 ms time constant, 42 s scan time, and 100 Gauss scan range, and 3410 G center field.

Figure 20:
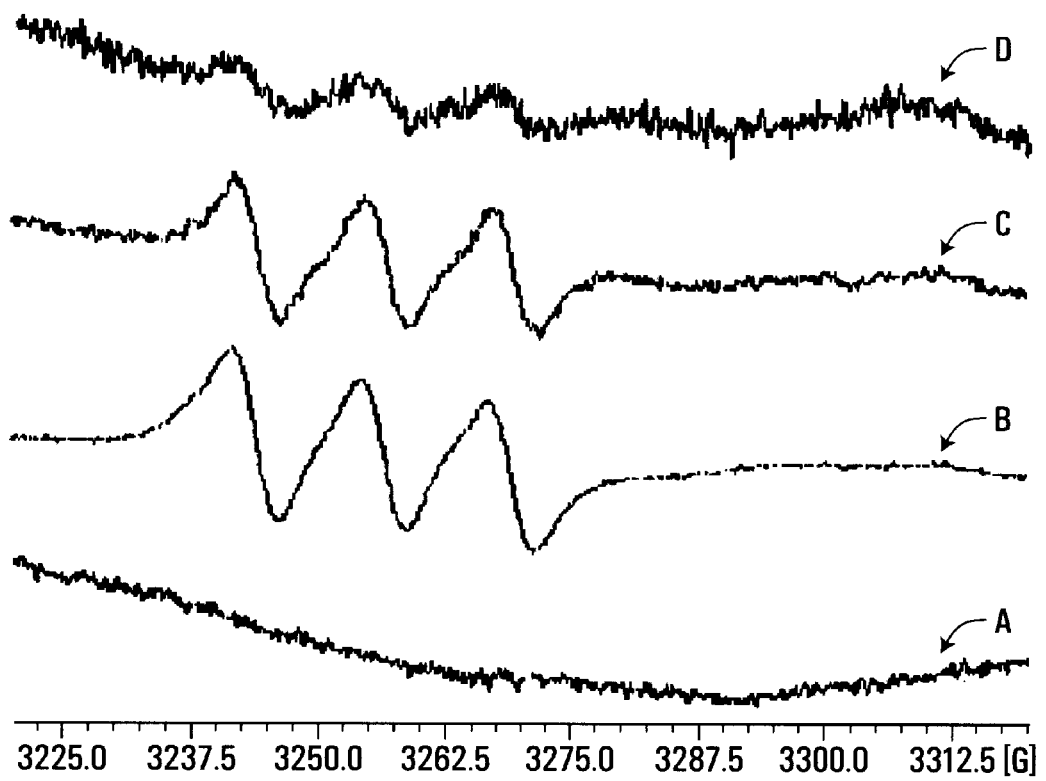
FIG. 20 shows results of an Electron Paramagnetic Resonance (EPR) assay using a compound of the invention on different tissue homogenates compared to a control and a NO standard.

FIG. 20 is a compilation of the spectra obtained. Curve A represents a blank control sample (the homogenate and NO spin-trap for the EPR assay, without the addition of MyoNovin). Curve B is an NO standard (homogenate and NO spin-trap for the EPR assay, bubbled with NO gas). Curves C (liver) and D (back muscle) represent the tissue homogenate mixed with MyoNovin.

In each tissue, the level of NO in the EPR spectrum of the blank control homogenate (without MyoNovin) is stable and shows no peaks in this range (3225 to 3312.5 G). For the samples incubated with MyoNovin, the EPR spectrum (here at 1 hour after adding MyoNovin) shows the presence of nitric oxide as is evident on comparison to the NO standard curve B. Thus, NO was strongly released by both tissue homogenates after the addition of MyoNovin and trapped in a stable form by the MGD spin-trap molecule (after Jung et al., Magn. Reson. Chem. 2005; 43: Spec. No.: S84-95, and Zhou et al., Biotechnology Techniques 1999; 13: 507-511).

By comparison the blank control homogenate shows no peaks, indicating there is a very low (undetectable) level of NO released from the tissue alone, in the absence of MyoNovin.

Therefore the EPR spectroscopy experiments confirm that MyoNovin induces a strong release of NO in skeletal muscle and liver muscle, and supports the idea that MyoNovin acts in vivo in a living system on skeletal muscle via NO release.

Figure 21:
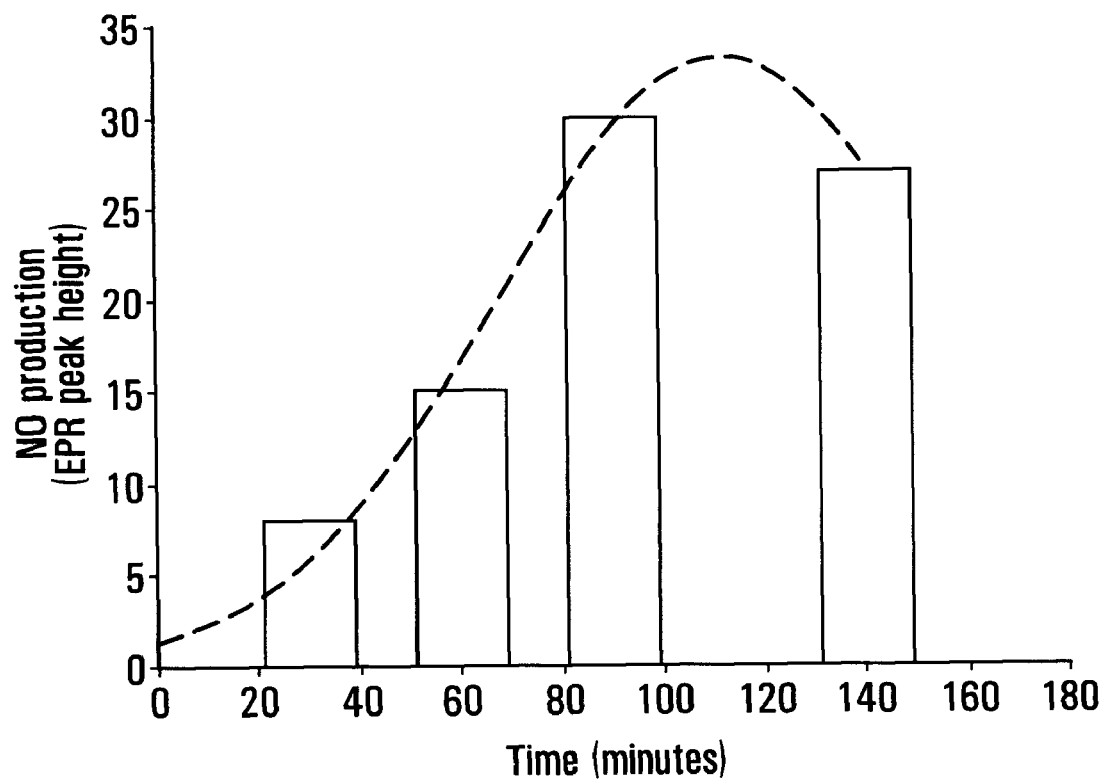
FIG. 21 shows the time-course of the NO release of FIG. 20 with a superimposed non-linear regression curve.

The time-course of NO release from the EPR studies on back muscle homogenates was also plotted and is shown in FIG. 21, together with a superimposed non-linear regression curve. FIG. 21 suggests a long lasting effect of MyoNovin as NO was released over a course of more than two hours. This could be very beneficial in some therapies where a sustained release is desirable.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

All publications, patents and patent applications cited in this specification are incorporated herein by reference as if each individual publication, patent or patent application were specifically and individually indicated to be incorporated by reference. The citation of any publication, patent or patent application is for its disclosure prior to the filing date and should not be construed as an admission that the present invention is not entitled to antedate such publication, patent or patent application by virtue of prior invention, nor should such citation be construed as an admission that such publication, patent or patent application is prior art.

It must be noted that as used in the specification and the appended claims, the singular forms of "a", "and" "the" include plural reference unless the context clearly indicates otherwise.

Unless defined otherwise all technical and scientific terms used herein have the same meaning as commonly understood to one of ordinary skill and the art to which this invention belongs.

The invention claimed is:

1. A pharmaceutical composition comprising a combination of methocarbamol and 1,2-di-O-nitro-3(o-methoxyphenoxy)-propanediol; and a pharmaceutically acceptable diluent or carrier.

2. A pharmaceutical composition of claim 1 for: promoting muscle cell proliferation or repair in normal muscle in need thereof, regulating satellite cell proliferation in dystrophic muscle or treating muscular dystrophy.

3. The pharmaceutical composition of claim 1 suitable for transdermal delivery.

4. The pharmaceutical composition of claim 1, which is a parenteral formulation, an oral dosage form, an intraperitoneal formulation, an intra-uterine formulation, an intrapleural formulation, a suppository for use vaginally or rectally, an inhalant formulation, a controlled-release implant or a patch.

5. The compound of formula:

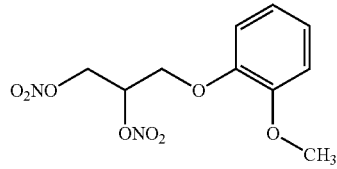

6. A commercial package comprising the pharmaceutical composition of claim 1 and instructions for the use thereof for promoting muscle cell proliferation repair in normal muscle in need thereof, for regulating satellite cell proliferation in dystrophic muscle or for treating muscular dystrophy.

7. A method for promoting formation of muscle tissue or repair of damaged muscle tissue, the method comprising administering an effective amount of a pharmaceutical composition of claim 1 to a subject in need of formation of muscle tissue or repair of damaged muscle tissue.

8. A method for facilitating transdermal delivery of 1,2-di-O-nitro-3(o-methoxyphenoxy)-propanediol to a target site in a subject, the method comprising applying methocarbamol to a skin region on the site along with application of 1,2-di-O-nitro-3(o-methoxyphenoxy)-propanediol.

9. The method of claim 7, wherein the subject suffers from a skeletal muscle injury or muscular dystrophy.

10. The method of claim 7, wherein the subject is a human or a non-human animal.

11. A method for making the compound of formula:

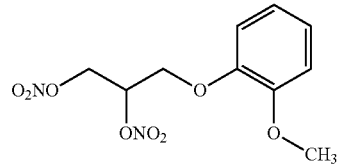

comprising dinitrosylating guaifenesin.

12. The method of claim 8, wherein the subject suffers from a skeletal muscle injury or muscular dystrophy.

13. The method of claim 8, wherein the subject is a human or a non-human animal.

* * * * *